(12) United States Patent
Yokoo et al.

(10) Patent No.: US 9,527,866 B2
(45) Date of Patent: Dec. 27, 2016

(54) PROCESSES FOR PRODUCTION OF INTERMEDIATES FOR 2-ALKYL CEPHEM COMPOUNDS

(71) Applicant: SHIONOGI & CO., LTD., Osaka-shi, Osaka (JP)

(72) Inventors: Katsuki Yokoo, Toyonaka (JP); Shinya Hisakawa, Toyonaka (JP); Kenji Yamawaki, Toyonaka (JP); Toshiaki Aoki, Toyonaka (JP); Yutaka Yokota, Toyonaka (JP); Masatoshi Takeo, Iwate (JP); Mikito Asai, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 14/439,113

(22) PCT Filed: Oct. 29, 2013

(86) PCT No.: PCT/JP2013/079803
§ 371 (c)(1),
(2) Date: Apr. 28, 2015

(87) PCT Pub. No.: WO2014/069649
PCT Pub. Date: May 8, 2014

(65) Prior Publication Data
US 2015/0291619 A1    Oct. 15, 2015

Related U.S. Application Data

(60) Provisional application No. 61/719,523, filed on Oct. 29, 2012, provisional application No. 61/720,520, filed on Oct. 31, 2012.

(51) Int. Cl.
*C07D 501/16* (2006.01)
*C07D 501/59* (2006.01)

(52) U.S. Cl.
CPC ........... *C07D 501/16* (2013.01); *C07D 501/59* (2013.01); *C07B 2200/13* (2013.01)

(58) Field of Classification Search
CPC .......................... C07D 501/16; C07D 501/59
USPC ........................................................ 544/47
See application file for complete search history.

(56) References Cited

U.S. PATENT DOCUMENTS

| | | |
|---|---|---|
| 3,487,079 A | 12/1969 | Sheehan |
| 3,660,396 A | 5/1972 | Wright |
| 4,081,595 A | 3/1978 | Nagata et al. |
| 4,463,172 A | 7/1984 | Horii et al. |
| 5,143,910 A | 9/1992 | Onoue et al. |
| 2011/0190254 A1 | 8/2011 | Nishitani et al. |
| 2013/0079319 A1 | 3/2013 | Yamawaki et al. |
| 2013/0096299 A1 | 4/2013 | Kusano et al. |
| 2013/0102583 A1 | 4/2013 | Hisakawa et al. |

FOREIGN PATENT DOCUMENTS

| | | |
|---|---|---|
| EP | 0035357 A1 | 9/1981 |
| EP | 0472060 A2 | 2/1992 |
| EP | 1489084 A1 | 12/2004 |
| EP | 2341053 A1 | 7/2011 |
| JP | 2-15090 | 1/1990 |
| JP | 2-28185 | 1/1990 |
| JP | 2-28187 | 1/1990 |
| JP | 2-117678 | 5/1990 |
| JP | 4-364189 | 12/1992 |
| JP | 5-213971 | 8/1993 |
| WO | 92/21683 A1 | 12/1992 |
| WO | 03/078440 A1 | 9/2003 |
| WO | 2007/096740 A2 | 8/2007 |
| WO | 2007/119511 A1 | 10/2007 |
| WO | 2010/050468 A1 | 5/2010 |

(Continued)

OTHER PUBLICATIONS

Mizokami et al. Chemical & Pharmaceutical Bulletin (1983), 31(5), 1482-93.*
Form PCT/IB/373, International Preliminary Report on Patentability Chapter 1 (May 5, 2015).
Form PCT/ISA/237, Written Opinion of the International Search Authority (Dec. 24, 2013).
Lei et al. Chinese Journal of Antibiotics, vol. 34, Issue 4, pp. 226-230 (2009), with English abstract.

(Continued)

*Primary Examiner* — Kahsay Habte
(74) *Attorney, Agent, or Firm* — Hamre, Schumann, Mueller & Larson, P.C.

(57) ABSTRACT

The invention relates to processes for the production of intermediates for preparing 2-alkyl cephem compounds useful as antimicrobial drugs. The invention provides a process which comprises oxidating a compound of the formula (I) or a salt thereof to give a compound of the formula (II) or a salt thereof wherein each symbol is as defined in the specification.

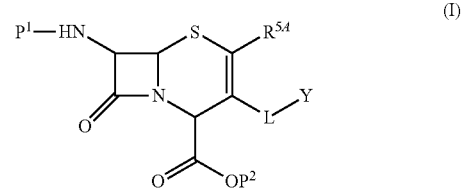

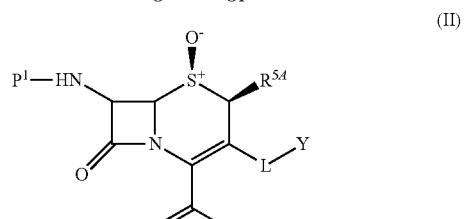

31 Claims, 3 Drawing Sheets

(56) References Cited

FOREIGN PATENT DOCUMENTS

| WO | 2011/125966 A1 | 10/2011 |
|---|---|---|
| WO | 2011/125967 A1 | 10/2011 |
| WO | 2011/136268 A1 | 11/2011 |

OTHER PUBLICATIONS

Mizokami et al. Chemical & Pharmaceutical Bullentin, vol. 31, No. 5, pp. 1482-1493 (1983).
Wright et al. Journal of Medicinal Chemistry, vol. 14, No. 5, pp. 420-425 (1971).
Vilrudachalam et al. International Journal of Peptide & Protein Research, vol. 10, pp. 51-59 (1977).
Waddell et al. Tetrahedron Letters, vol. 37, No. 12, pp. 1971-1974 (1996).
Gunda. Liebigs Annalen der Chemie, vol. 3, pp. 311-312 (1990).
Pitlik et al. Journal of Heterocycle Chemistry, vol. 26, No. 2, pp. 461-464 (1989).
Spry. Tetrahedron Letters, vol. 21, No. 14, pp. 1289-1292 (1980).
Hagmann et al. European Journal of Medicinal Chemistry, vol. 24, No. 6, pp. 599-604 (1989).
Mobashery et al. Journal of Organic Chemistry, vol. 51, pp. 4723-4726 (1986).
Bugarin et al. Chemical Communications, vol. 46, pp. 1715-1717 (2010).
Maejima et al. Anticibrobial Agents and Chemotherapy, vol. 35, No. 1, pp. 104-110 (1991).
Watanabe et al. Anticibrobial Agents and Chemotherapy, vol. 39, No. 12, pp. 2787-2791 (1995).
Yamano et al. Applied Micorbiology and Biotechnology, vol. 40, p. 892-897 (1994).
Takeda et al. The Journal of Antibiotics, vol. 61, No. 1, pp. 36-39 (2008).
Hashizume et al. The Journal of Antibiotics, vol. 43, No. 12, pp. 1671-1620 (1990).
Weissberger et al. The Journal of Antibiotics, vol. 42. No. 5, pp. 795-806 (1989).
Yamano et al. Applied Microbiology and Biotechnology, vol. 40, No. 6, pp. 892-897 (1994).
Shibahara et al. The Journal of Antibiotics, vol. 41, pp. 1154-1157 (1988).
Okonogi et al. The Journal of Antibiotics, vol. 43, No. 4, pp. 357-371 (1989).
International Search Report issued in PCT/JP2013/079803, mailed Dec. 24, 2013.
Halligan et al. "Radical Rearrangement: A Strategy for Conversion of Cephalosporin to 1-Carba(dethia) cephalosporin". Tetrahedron, vol. 56, No. 31, pp. 5679-5685, Jul. 28, 2000.
Extended European Search Report issued in corresponding European Patent Application on May 3, 2016 (9 pages).

* cited by examiner

PROCESSES FOR PRODUCTION OF INTERMEDIATES FOR 2-ALKYL CEPHEM COMPOUNDS

TECHNICAL FIELD

The invention relates to processes of intermediates for preparing 2-alkyl cephem compounds useful as antimicrobial drugs.

BACKGROUND ART

To date, a variety of cephem compounds have been developed as antimicrobial drugs. Among them, same 2-alkylcephem compounds are reported (Patent Documents 1, 2 and Non-Patent Documents 1 to 4), however, 2-stereoselective synthesis thereof was very difficult. Thus, an efficient method for stereoselectively producing 2-alkylcephem compounds has been desired.

PRIOR ART DOCUMENT

Patent Document

[Patent Document 1] EP 0035357 A1
[Patent Document 2] U.S. Pat. No. 3,487,079

Non-Patent Document

[Non-Patent document 1] Chemical & Pharmaceutical Bulletin, vol. 31, 1482-1493 (1983)
[Non-Patent document 2] Journal of Medicinal Chemistry, vol. 14, 420-425 (1971)
[Non-Patent document 3] International Journal of Peptide & Protein Research, vol. 10, 51-59 (1977)
[Non-Patent document 3] Tetrahedron Letter, vol. 37, 1971-1974 (1996)

SUMMARY OF INVENTION

Problems to be Solved by the Invention

The subject invention provides processes for the production of intermediates for the synthesis of 2-alkyl cephems compounds, in particularly, a process for selectively producing 2-methyl cephems compounds in high yield.

Means for Solving the Problem

The subject invention provides the following inventions:
1. A process for preparing a compound of the formula (II) or a salt thereof,

[Chemical Formula 1]

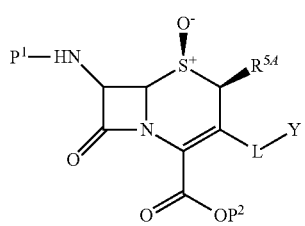

(II)

wherein,
$R^{5A}$ is lower alkyl;
Y is a leaving group;
L is a single bond, lower alkylene or lower alkenylene;
$P^1$ is acyl or an amino-protecting group;
$P^2$ is a carboxy-protecting group;
which comprises:
oxidation of a compound of the formula (I) or a salt thereof,

[Chemical Formula 2]

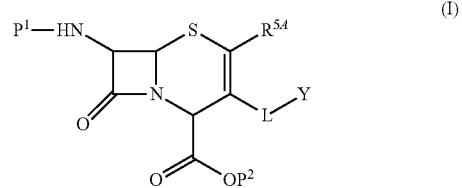

(I)

wherein, each symbol is as defined above,
to give a compound of the formula (II) or a salt thereof.
2. A process for preparing a compound of the formula (II) or a salt thereof,

[Chemical Formula 3]

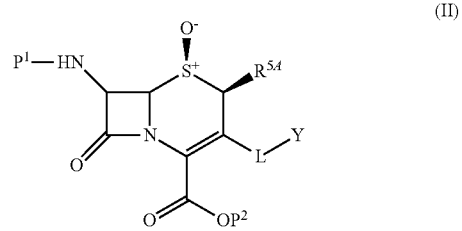

(II)

wherein,
$R^{5A}$ is lower alkyl;
Y is a leaving group;
L is a single bond, lower alkylene or lower alkenylene;
$P^1$ is acyl or an amino-protecting group;
$P^2$ is a carboxy-protecting group;
which comprises:
reacting a compound of the formula (IV) or a salt thereof,

[Chemical Formula 4]

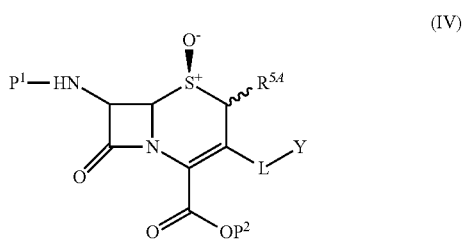

(IV)

wherein,
the wavy line means that the bond is a mixture of α-configuration and β-configuration;
the other symbols are as defined above,
with a base to give a compound of the formula (II) or a salt thereof.

3. A process for preparing a compound of the formula (II) or a salt thereof,

[Chemical Formula 5]

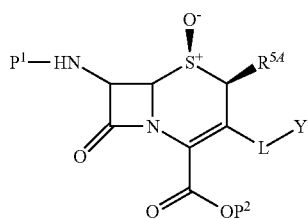

(II)

wherein,
- $R^{5A}$ is lower alkyl;
- Y is a leaving group;
- L is a single bond, lower alkylene or lower alkenylene;
- $P^1$ is acyl or an amino-protecting group;
- $P^2$ is a carboxy-protecting group;

which comprises:
oxidation of a compound of the formula (I) or a salt thereof,

[Chemical Formula 6]

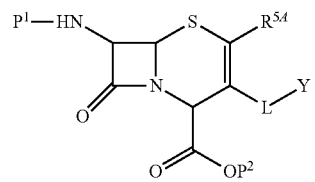

(I)

wherein, each symbol is as defined above,
to give a compound of the formula (V) or a salt thereof,

[Chemical Formula 7]

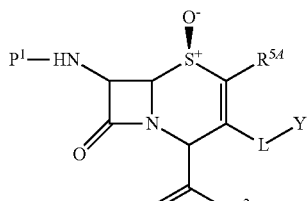

(V)

wherein each symbol is as defined above, and
isomerization of a compound of the formula (V) to a compound of the formula (II) or a salt thereof.

4. A process for preparing a compound of the formula (XVI) or a salt thereof,

[Chemical Formula 8]

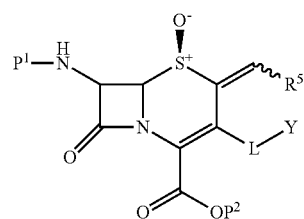

(XVI)

wherein,
- $R^5$ is hydrogen or lower alkyl;
- the other symbols are as defined above,
- the wavy line means that the bond is in cis or trans configuration, or a mixture thereof; provided that "-L-Y" is not —$CH_2$—O—C(=O)—$CH_3$, which comprises:
reacting aldehyde, amine and a compound of the formula (XV) or a salt thereof,

[Chemical Formula 9]

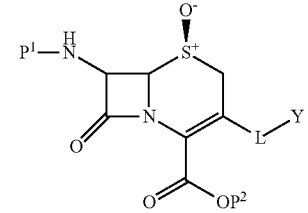

(XV)

wherein, each symbol is as defined above,
to give a compound of the formula (XVI) or a salt thereof.

5. A process for preparing a compound of the formula (II) or a salt thereof,

[Chemical Formula 10]

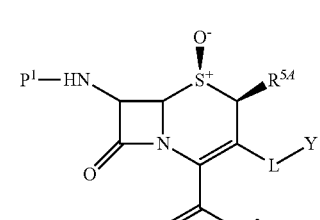

(II)

wherein, each symbol is as defined above;

which comprises:
reduction of a compound of the formula (XVI) or a salt thereof,

[Chemical Formula 11]

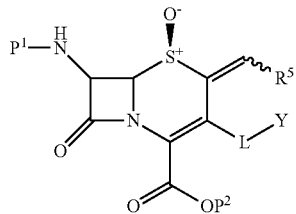

(XVI)

wherein, each symbol is as defined above,
to give a compound of the formula (II) or a salt thereof.

6. A process for preparing a compound of the formula (III) or a salt thereof,

[Chemical Formula 12]

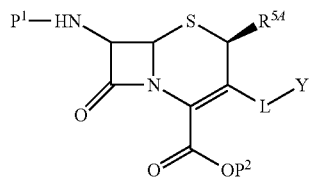

(III)

wherein,
$R^{5A}$ is lower alkyl;
Y is a leaving group;
L is a single bond, lower alkylene or lower alkenylene;
$P^1$ is acyl or an amino-protecting group;
$P^2$ is a carboxy-protecting group;
which comprises:
reduction of a compound of the formula (II) or a salt thereof,

[Chemical Formula 13]

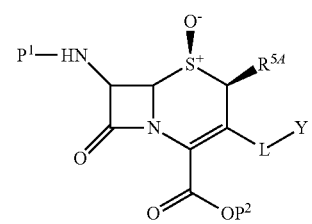

(II)

wherein each symbol is as defined above,
to give a compound of the formula (III) or a salt thereof.

7. A process for preparing a compound of the formula (III) or a salt thereof according to the above 6, from a compound of the formula (II) or a salt thereof obtained by the process according to any one of the above 1 to 3 and 5.

8. A process for preparing a compound of the formula (II) or a salt thereof according to the above 5, wherein the compound of the formula (XVI):

[Chemical Formula 14]

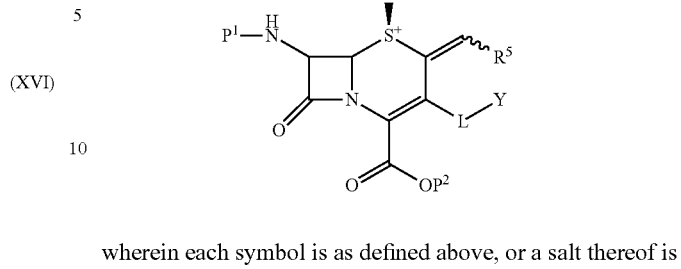

(XVI)

wherein each symbol is as defined above, or a salt thereof is obtained by the process which comprises:
reacting aldehyde, amine and a compound of the formula (XV) or a salt thereof,

[Chemical Formula 15]

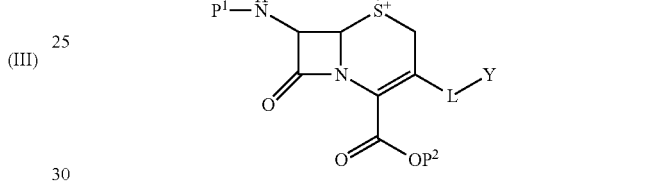

(XV)

wherein, each symbol is as defined above,
to give a compound of the formula (XVI) or a salt thereof.

9. A process of any one of the above 1 to 3 and 5 to 8, wherein $R^{5A}$ is methyl.

10. A process of anyone of the above 1 to 9, wherein L is —$CH_2$—.

11. A process of any one of the above 1 to 9, wherein L is a single bond.

12. A process of any one of the above 1 to 11, wherein Y is halogen.

13. A process of any one of the above 1 to 12, wherein $P^1$ is acyl.

14. A process of any one of the above 1 to 13, wherein $P^2$ is optionally substituted aralkyl.

15. A process for preparing a compound of the formula (I-1) or a salt thereof,

[Chemical Formula 16]

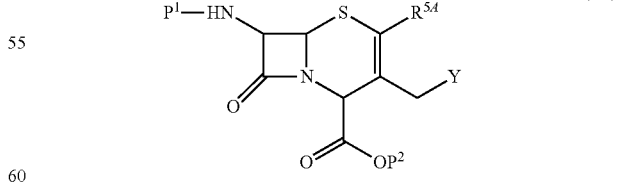

(I-1)

wherein,
$R^{5A}$ is lower alkyl;
Y is a leaving group;
$P^1$ is acyl or an amino-protecting group;
$P^2$ is a carboxy-protecting group;

which comprises:
reacting a compound of the formula (VI) or a salt thereof,

[Chemical Formula 17]

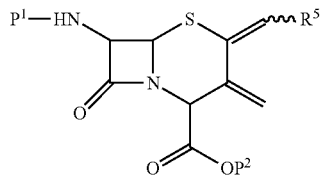

(VI)

wherein, each symbol is as defined above;
with an acid to give a compound of the formula (I-1) or a salt thereof.

16. A process for preparing a compound of the formula (VII) or a salt thereof,

[Chemical Formula 18]

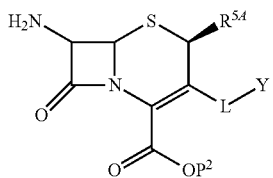

(VII)

wherein, each symbol is as defined above,
which comprises:
deprotection of a compound of compound (III) or a salt thereof obtained by the process according to the above 6, to give a compound of the formula (VII) or a salt thereof.

17. A compound of the formula or a salt thereof,

[Chemical Formula 10]

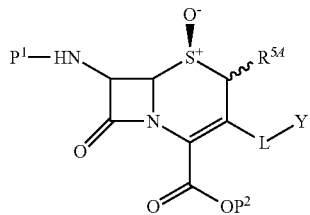

(IV)

wherein
the wavy line means that the bond is a mixture of α-configuration and β-configuration;
the other symbols are as defined above, excluding the following;
1) L is a single bond and Y is halogen; and
2) L is lower alkylene or lower alkenylene and Y is acetyl.

18. A compound of the formula or a salt thereof,

[Chemical Formula 20]

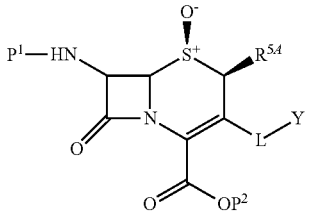

(II)

wherein each symbol is as defined above, excluding the following;
1) L is a single bond and Y is halogen; and
2) L is lower alkylene or lower alkenylene and Y is acetyl.

19. A compound of the formula or a salt thereof,

[Chemical Formula 21]

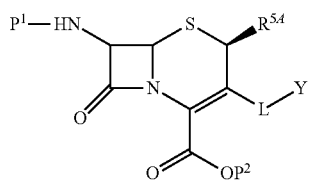

(III)

wherein each symbol is as defined above, excluding the following;
1) L is a single bond and Y is halogen; and
2) L is lower alkylene or lower alkenylene and Y is acetyl.

20. A compound of the formula or a salt thereof,

[Chemical Formula 22]

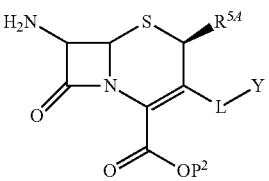

(VII)

wherein each symbol is as defined above, excluding the following;
1) L is a single bond and Y is halogen; and
2) L is lower alkylene or lower alkenylene and Y is acetyl.

21. A compound of the formula or a salt thereof,

[Chemical Formula 23]

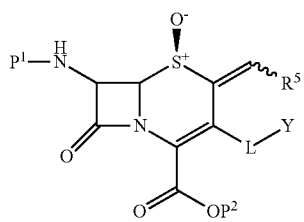

(XVI)

wherein

L is lower alkylene or lower alkenylene;

Y is halogen;

$R^5$ is hydrogen;

the wavy line means that the bond is in cis or trans configuration, or a mixture thereof;

the other symbols are as defined above.

22. A compound according to any one of the above 17 to 20, wherein Y is methanesulfonyloxy, trifluoromethanesulfonyloxy or p-toluenesulfonyloxy; L is a single bond; and $R^{5A}$ is methyl.

23. A compound according to any one of the above 17 to 20, wherein

Y is halogen; L is —$CH_2$—; and $R^{5A}$ is methyl.

24. A method for transforming 2-α-alkyl-cephem compound to 2-β-alkyl-cephem compound, which comprises reaction of the 2-α-methyl-cephem compound with a base.

25. A crystal of the following compound (XVI-2):

[Chemical Formula 24]

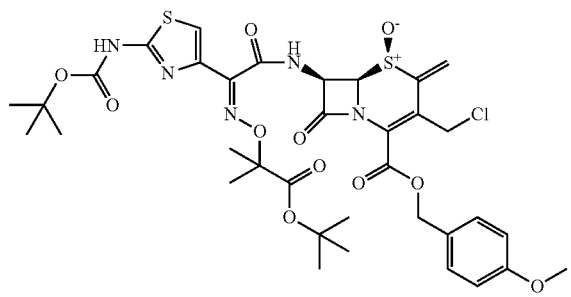

XVI-2 or solvate thereof.

26. The crystal of the above 25, having a diffraction pattern in powder X-ray diffraction showing main peaks at diffraction angle (2θ)=5.3±0.2°, 7.0±0.2°, 10.2±0.2°, 14.7±0.2°, 15.8±0.2°, 17.4±0.2°, 21.1±0.2°, and 21.3±0.2°.

27. A crystal of the following compound (II-3):

[Chemical Formula 25]

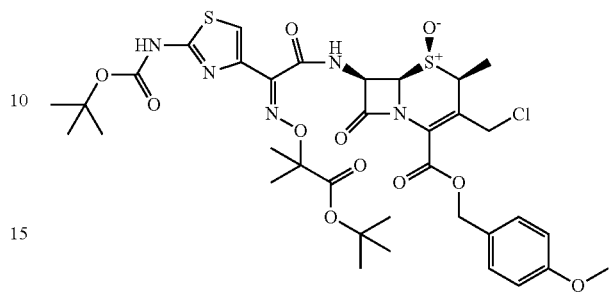

II-3 or solvate thereof.

28. The crystal of the above 27, having a diffraction pattern in powder X-ray diffraction showing main peaks at diffraction angle (2θ)=5.7±0.2°, 7.8±0.2°, 11.3±0.2°, 14.5±0.2°, 20.8±0.2°, and 21.6±0.2°.

29. A crystal of the following compound (III-2):

[Chemical Formula 26]

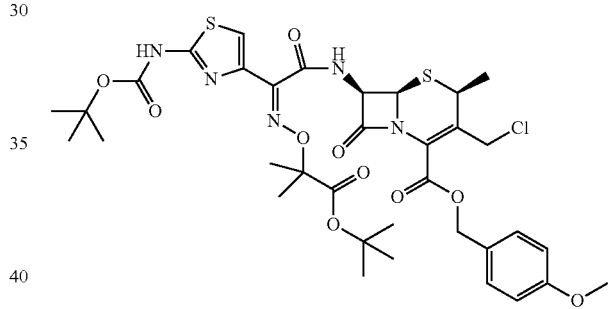

III-2 or solvate thereof.

30. The crystal of the above 29, having a diffraction pattern in powder X-ray diffraction showing main peaks at diffraction angle (2θ)=4.8±0.2°, 7.7±0.2°, 8.1±0.2°, 9.1±0.2°, 9.6±0.2°, 11.4±0.2°, 14.9±0.2°, 16.9±0.2°, 19.3±0.2° and 20.2±0.2°

Effects of the Invention

The processes and intermediates of the subject invention are useful as an industrial production of 2-alkyl cephem compounds. By using the present invention, a variety of 2-alkyl cephem compounds or their derivatives can be synthesized efficiently and conveniently, e.g., in short steps, in high yield, in high purity, in high selectivity, and/or under mild conditions.

DESCRIPTION OF EMBODIMENTS

Figure 1:
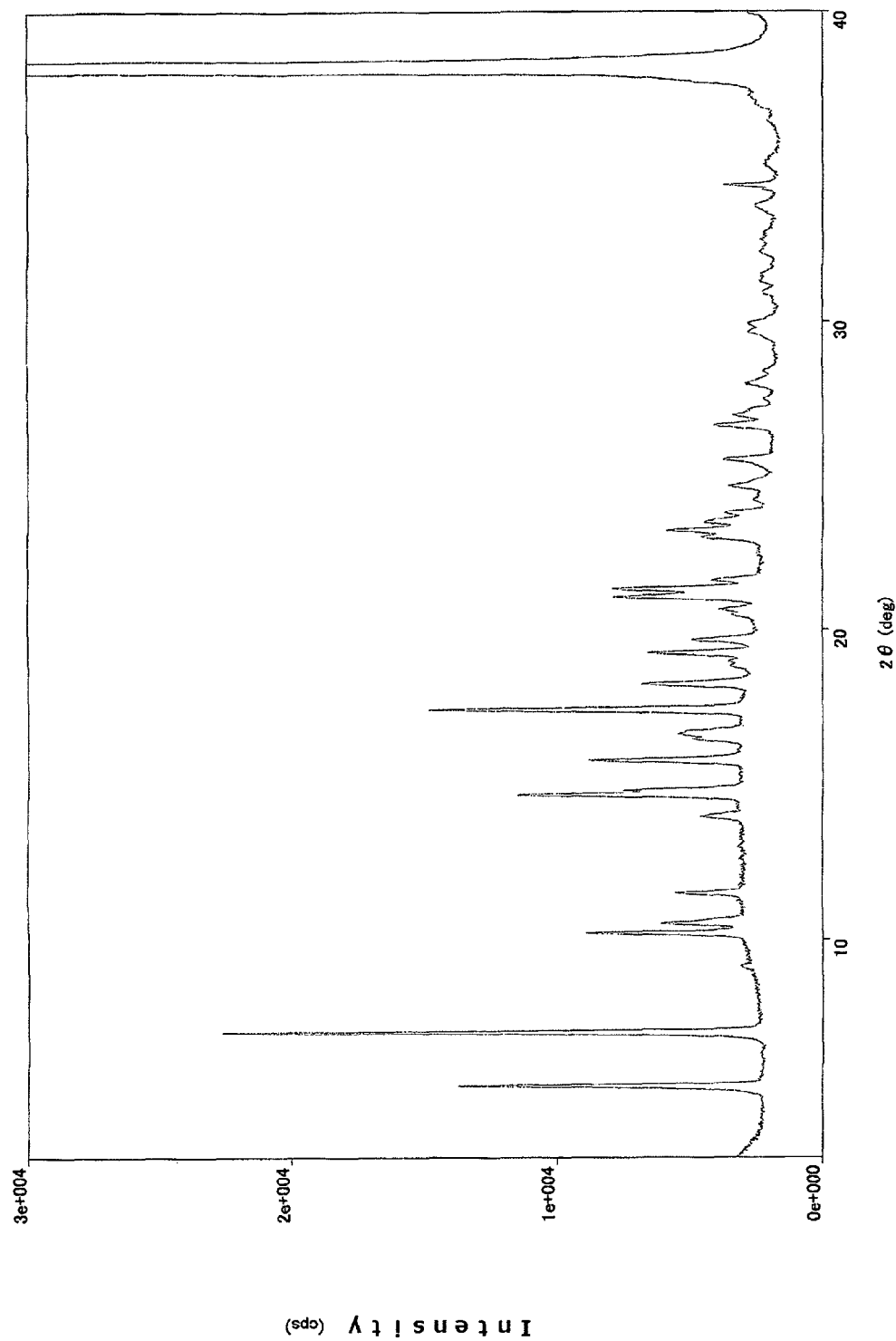
FIG. 1 shows a powder X-ray diffraction pattern of the crystal of compound XVI-2 obtained in (2) of Example 7. The vertical axis is intensity (cps), and the horizontal axis is 2-theta angles (degree). The peak at about 38 degree is Al peak as the sample holder.
Figure 2:
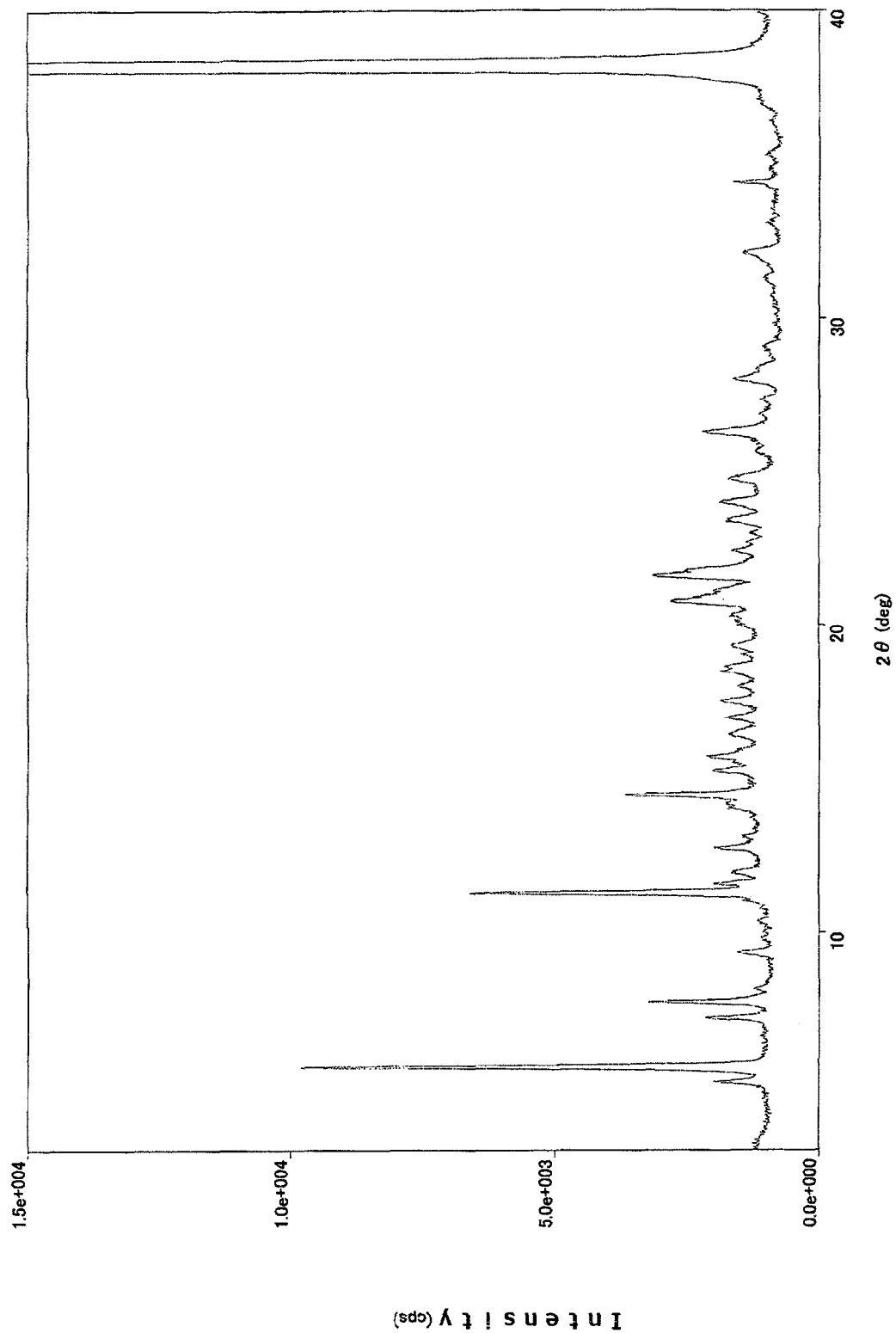
FIG. 2 shows a powder X-ray diffraction pattern of the crystal of compound II-3 obtained in (4) of Example 7. The vertical axis is intensity (cps), and the horizontal axis is 2-theta angles (degree). The peak at about 38 degree is Al peak as the sample holder.
Figure 3:
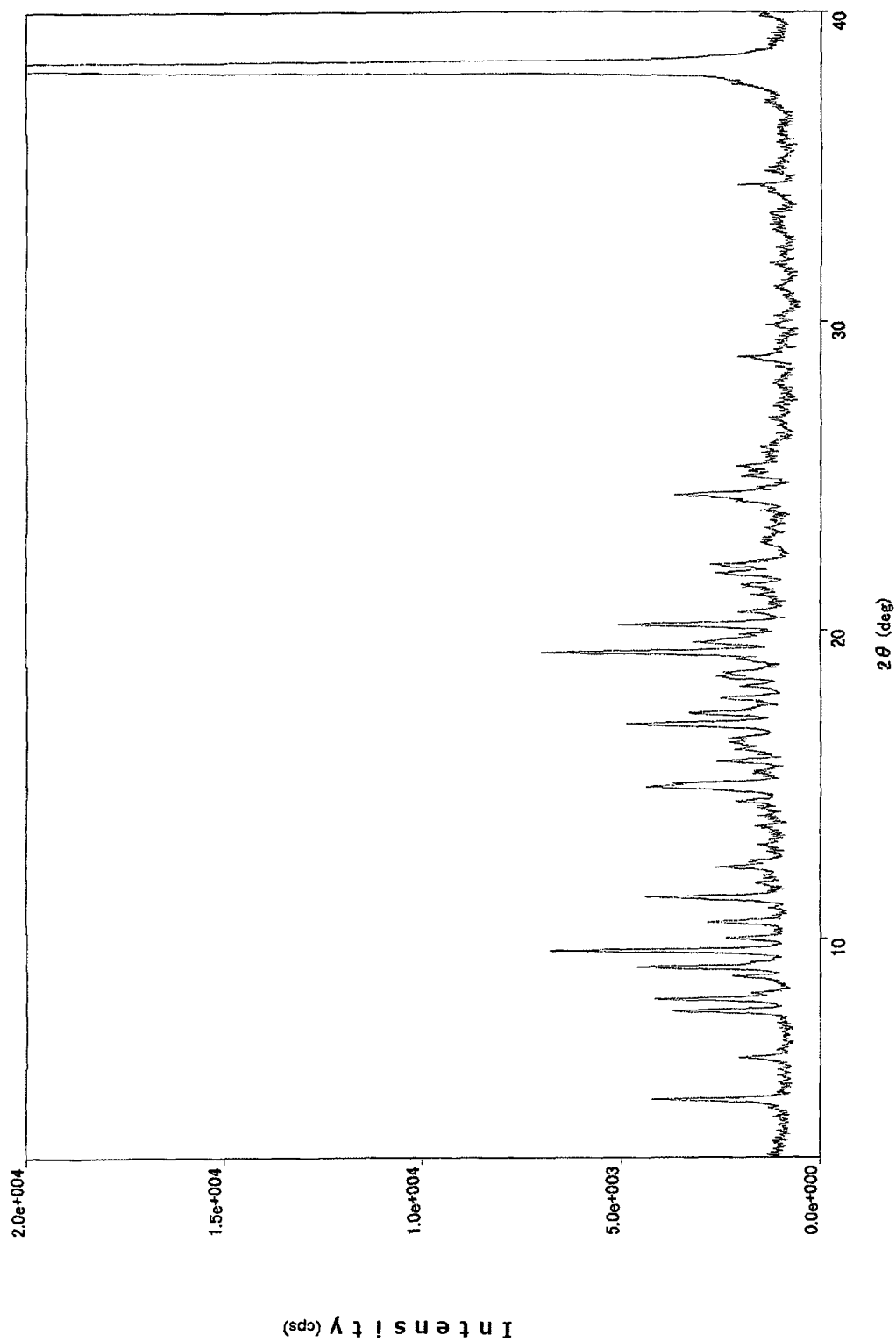
FIG. 3 shows a powder X-ray diffraction pattern of the crystal of compound III-2 obtained in (7) of Example 7. The vertical axis is intensity (cps), and the horizontal axis is 2-theta angles (degree). The peak at about 38 degree is Al peak as the sample holder.

It should be understood that, throughout the present specification, the expression of a singular form (e.g., "a", "an", "the", and the like; and in other languages, corresponding articles, adjectives, and the like) includes the concept of its plural form unless specified otherwise. Furthermore, it should be understood that the terms used herein are used in a meaning generally used in the art unless specified otherwise. Thus, unless defined otherwise, all technical and scientific terms used herein have the same meaning as those generally understood by those skilled in the art in the field to which the subject invention pertains. Each specific definition of terms specifically used herein is described below.

Each term used herein means, alone or in combination with another word, as below.

"Halogen" includes fluorine, chlorine, bromine and iodine. Preferably, halogen is fluorine, chlorine or bromine, and more preferably is chlorine.

"Lower alkyl" includes linear or branched alkyl having 1-8 carbons, preferably 1-6 carbons, and more preferably 1-4 carbons, for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, and the like. Preferred is methyl.

"Lower alkylene" includes linear alkylene having 1-8 carbons, preferably 1-6 carbons, more preferably 1-4 carbons, and most preferably one or two carbons, for example, methylene, ethylene, n-propylene, n-butylene, n-pentylene, n-hexylene, and the like.

"Lower alkenylene" includes linear alkenylene having 2-8 carbons, preferably 2-6 carbons, more preferably 2-4 carbons, and at least one double bond at any position, and includes, for example, vinylene, allylene, propenylene, butenylene, prenylene, butadienylene, pentenylene, pentadienylene, hexenylene, hexadienylene, and the like.

"Lower alkynylene" includes linear alkynylene having 2-8 carbons, preferably 2-6 carbons, more preferably 2-4 carbons, and at least one triple bond at any position, for example, ethynylene, propynylene, buthynylene, pentynylene, hexynylene, and the like.

"Lower alkoxy" includes linear or branched alkoxy having 1-8 carbons, preferably 1-6 carbons, and more preferably 1-4 carbons, for example, methoxy, ethoxy, n-propoxy, isopropoxy, n-butoxy, isobutoxy, sec-butoxy, tert-butoxy, n-pentoxy, isopentxy, neopentoxy, hexyoxy, isoheptyloxy, isoheptyloxy, n-octyloxy, n-octyloxy, and the like.

"Aralkyl" includes alkyl having one to three groups selected from above "aryl", preferably wherein carbon number of alkyl part is 1 or 4, more preferably is 1 or 2, for example, benzyl, phenethyl, phenylpropyl, trityl, and the like.

"Heteroaralkyl" includes alkyl having one to three groups selected from above "heteroaryl", preferably wherein carbon number of alkyl part is 1 or 4, more preferably is 1 or 2, for example, furylmethyl, thienylmethyl, pyrolylmethyl, pyridylmethyl, thienylethyl, furylethyl, imidazorylmethyl, benzotienylmethyl, thiazolylmethyl, and the like.

"Lower alkyl" of "tri-lower alkylsilyl" is as defined above, for example, trimethylsilyl, t-butyldimethylsilyl and the like.

"Acyl" includes formyl, optionally substituted lower alkylcarbonyl (e.g., acetyl, propionyl, butylyl, isobutylyl, valeryl, isovaleryl, pivaloyl, hexanoyl, octanoyl, methoxyethylcarbonyl, 2,2,2-trifluoroethylcarbonyl), optionally substituted alkenyloxycarbonyl (e.g., alloc, cinnamyloxy carbonyl), alkoxycarbonylacetyl (e.g., ethoxycarbonylmethylcarbonyl), (lower)alkoxy(lower)alkylcarbonyl (e.g., methoxyethylcarbonyl), (lower)alkylcarbamoyl(lower)alkylcarbonyl (e.g., methylcarbamoylethylcarbonyl), optionally substituted arylcarbonyl (e.g., benzoyl, toluoyl), optionally substituted cycloalkyloxy carbonyl (e.g., cycrohexyloxycarbonyl), optionally substituted aralkyloxy carbonyl (e.g., benzyloxycarbonyl, p-nitrobenzyloxycarbonyl), optionally substituted heteroaralkyl carbonyl (e.g., thienylmethyl carbonyl) and the like. Acyl includes a group of formula (P1-1) mentioned hereafter.

"Aryl" includes phenyl, naphthyl, anthryl, phenanthryl, and the like, and phenyl is preferable.

"Heterocyclic group" includes heterocyclic groups having at least one hetero atom arbitrarily selected from O, S, and N in the ring, and includes, for example, 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, triazolyl, thiadiazolyl, furyl, thienyl, and the like; bicyclic fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, pyrazolopyridine, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl, and the like; tricyclic fused heterocyclic groups such as carbazolyl, acridinyl, xanthenyl, phenothiadinyl, phenoxathiinyl, phenoxazinyl, dibenzofuryl, imidazoquinolyl, and the like; non-aromatic heterocyclic groups such as dioxanyl, thiiranyl, oxiranyl, oxathiolanyl, azetidinyl, thianyl, thiazolidine, pyrrolidinyl, pyrrolinyl, imidazolidinyl, imidazolinyl, pyrazolidinyl, pyrazolinyl, piperidyl, piperazinyl, morpholinyl, thiomorpholinyl, thiomorpholino, dihydropyridyl, dihyrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrahydrodiazepinyl, and the like. Preferably, the heterocyclic group is a 5- or 6-membered heteroaryl or non-aromatic heterocyclic group, and more preferably, a 5- or 6-membered heteroaryl.

The carboxy protecting groups is explained, for example, in Protective Groups in Organic Synthesis, written by T. W. Greene, John Wiley & Sons Inc. (1991), or the like. Examples thereof include lower alkyl (e.g., methyl, ethyl, t-butyl), (lower) alkylcarbonyloxymethyl (e.g., pivaloyl), optionally substituted aralkyl (e.g., benzyl, benzhydryl, phenethyl, p-methoxybenzyl, p-nitrobenzyl), silyl groups (t-butyldimethylsilyl, diphenyl (t-butyl) silyl), and the like.

The amino-protecting group is explained, for example, in Protective Groups in Organic Synthesis, written by T. W. Greene, John Wiley & Sons Inc. (1991), or the like.

Examples thereof include phthalimide, acyl (formyl, optionally substituted alkylcarbonyl (chloroacetyl, trichloroacetyl etc.), lower alkoxycarbonyl (butoxycarbonyl (Boc), benzyloxy carbonyl etc.), lower alkenyloxycarbonyl (allyloxycarbonyl (Alloc), etc.), optionally substituted aralkyloxycarbonyl (benzyloxycarbonyl, p-nitrobenzyloxycarbonyl etc.), optionally substituted heteroaralkylcarbonyl (thienylmethylcarbonyl etc.)), optionally substituted aralkanoyl (p-nitrobenzoyl, etc.), optionally substituted aralkyl (trityl, benzhydryl (BH) etc.), optionally substituted arylimino (N-benzylidene, N-salicylidene, N-2-methoxybenzylidene etc.), optionally substituted lower alkylimino (N-isopropylidene etc.) tri-lower alkylsilyl (trimethylsilyl, tert-butyldimethylsilyl etc.) and the like.

The hydroxy-protecting group is explained, for example, in Protective Groups in Organic Synthesis, written by T. W. Greene, John Wiley & Sons Inc. (1991), or the like. Examples thereof include lower alkoxycarbonyl such as a C1-C4 alkoxycarbonyl (e.g., t-butyloxycarbonyl), halogenated lower alkoxycarbonyl such as a halogenated (C1-C3) alkoxycarbonyl (e.g., 2-iodo ethyloxycarbonyl, 2,2,2-trichloroethyloxycarbonyl), aryl-(lower) alkoxycarbonyl such as a phenyl-(C1-C4) alkoxycarbonyl having optionally a substituent(s) on the benzene ring (benzyloxycarbonyl, o-nitrobenzyloxycarbonyl, p-nitrobenzyloxycarbonyl, p-methoxybenzyloxycarbonyl), p-methoxybenzyl (PMB), tri-lower alkylsilyl such as tri-(C1-C4) alkylsilyl (e.g., trimethylsilyl, t-butyldimethylsilyl), a substituted methyl such as C1-C4 alkoxymethyl (e.g., methoxymethyl), C1-C4 alkoxy-(C1-C4) alkoxymethyl (e.g., 1-methoxyethoxymethyl), C1-C4 alkylthiomethyl (e.g., methylthiomethyl), tetrahydropyranyl, and the like.

Salts include, for example, salts formed with alkali metal (e.g. lithium, sodium, potassium, etc.), alkaline earth metal (e.g. calcium, barium, etc.), magnesium, transition metal (e.g. zinc, ferrum, etc.), ammonia, organic base (e.g. trimethylamine, triethylamine, dicyclohexylamine, ethanolamine, diethanolamine, triethanolamine, meglumine, diethanolamine, ethylenediamine, pyridine, picoline, quinoline, etc.) and amino acid, or salts formed with inorganic acid (e.g. hydrochloric acid, sulphuric acid, nitric acid, carbonic acid, hydrobromic acid, phosphoric acid, hydroiodic acid, etc.), and organic acid (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulphonic acid, p-toluenesulfonic acid, methanesulphonic acid, ethanesulphonic acid, etc, particularly, salts formed with hydrochloric acid, sulphuric acid, phosphoric acid, tartaric acid, methanesulphonic acid. These salts can be formed according to the conventional method. These salts may be solvate such as hydrate and alcholate.

The leaving group includes halogen (Cl, Br, I, F), acetoxy, substituted sulfonyloxy (e.g., methanesulfonyloxy, optionally substituted benzensulfonyloxy (e.g., benzenesulfonyloxy, p-toluenesulfonyloxy) trifluoromethanesulfonyloxy), and the like. Preferred is halogen (Cl, Br, I), acetoxy, methanesulfonyloxy p-toluenesulfonyloxy or trifluoromethanesulfonyloxy. More preferred is halogen (Cl, Br, I), acetoxy, methanesulfonyloxy, p-toluenesulfonyloxy.

The intermediates of the present invention may be reacted with a variety of materials for forming each side chain moiety at the 3-, 4- and/or 7-position of the cephem skeleton, if necessary in combination with the deprotection of an amino-protecting group and/or a carboxy-protecting group, to obtain various 2-alkyl cephem compounds.

When $P^1$ is acyl, preferred is the group represented by the following formula:

[Chemical Formula 27]

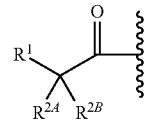

(P1-1)

wherein, $R^1$ is an optionally substituted carbocyclic group, an optionally substituted aryloxy, an optionally substituted heterocyclic group or an optionally substituted heteroaryloxy;

with regard to $R^{2A}$ and $R^{2B}$, a) $R^{2A}$ is hydrogen, optionally substituted amino, —$SO_3H$, optionally substituted amino sulfonyl, carboxyl, optionally substituted (lower alkyl) oxycarbonyl, optionally substituted carbamoyl, hydroxyl, or substituted carbonyloxy; and $R^{2B}$ is hydrogen, provided that $R^{2A}$ and $R^{2B}$ are not hydrogen at the same time, or b) $R^{2A}$ and $R^{2B}$ are taken together to form optionally substituted methylidene or optionally substituted hydroxyimino.

Examples of "optionally substituted carbocyclic group", "optionally substituted aryloxy", "optionally substituted heteroaryloxy" or "optionally substituted heterocyclic group" of $R^1$ include phenyl, aminothiazole, aminothiadiazole, thiophene, furan, benzothiazole, pyridine, pyrimidine, pyridazine, aminopyridine, phenoxy, pyridiloxy, and the like, each optionally substituted with hydroxyl and/or halogen. Preferred Examples include the followings:

[Chemical Formula 28]

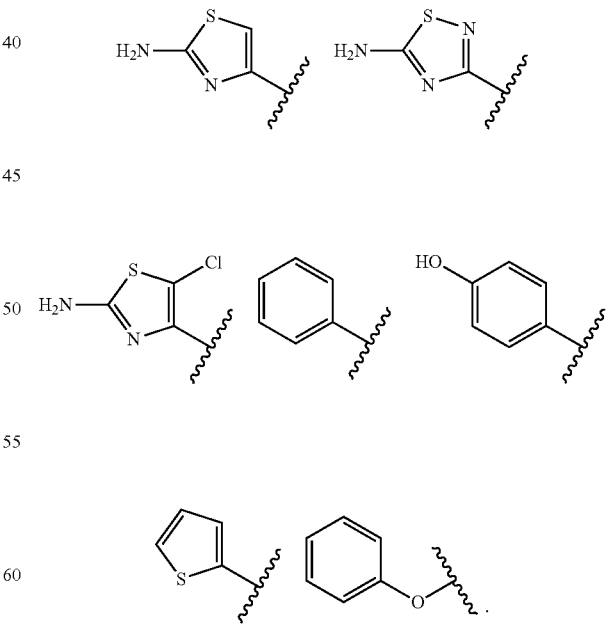

Examples of $R^{2A}$ include hydrogen, optionally substituted amino, —COOH, —$SO_3H$, optionally substituted aminosulfonyl, carboxyl, optionally substituted carbamoyl, hydroxyl, substituted carbonyloxy, and the like.

In a group of the above formula (P1-1), preferred is that $R^{2B}$ is hydrogen and $R^{2A}$ is the following group:

1) substituted amino group shown below:

[Chemical Formula 29]

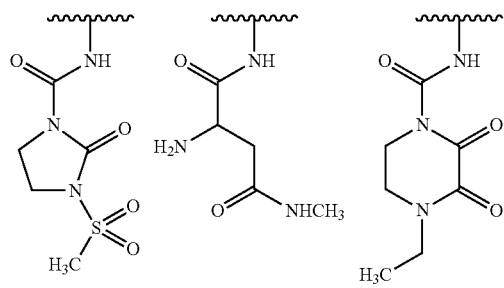

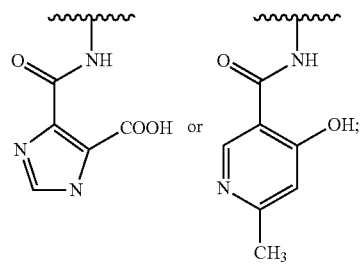

2) substituted aminosulfonyl group shown below:

[Chemical Formula 30]

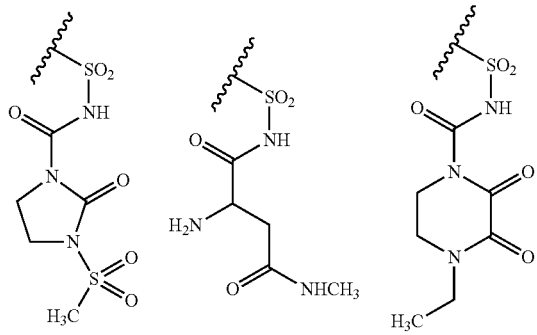

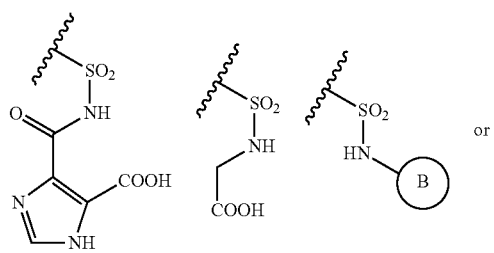

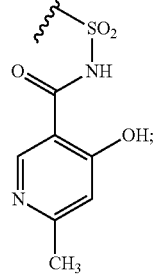

wherein ring B represents an optionally substituted heterocyclic group;

3) substituted carbamoyl group shown below:

[Chemical Formula 31]

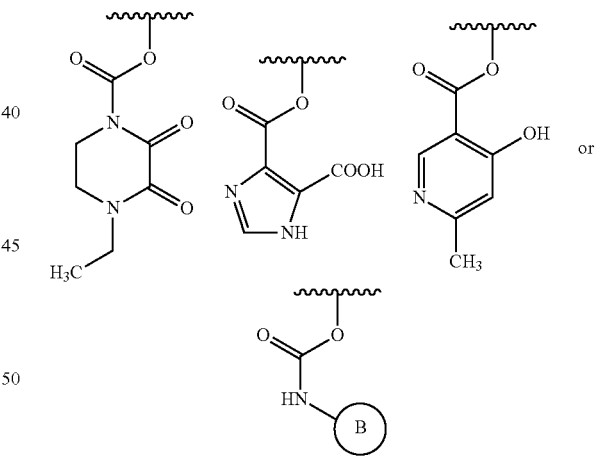

wherein ring B represents an optionally substituted heterocyclic group; or 4) substituted carbonyloxy shown below:

[Chemical Formula 32]

wherein ring B represents an optionally substituted.

Alternatively, $R^{2A}$ and $R^{2B}$ may be taken together to form a substituted methylidene group shown below:

[Chemical Formula 33]

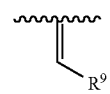

wherein $R^9$ is optionally substituted lower alkyl. Preferred is the group shown below:

[Chemical Formula 34]

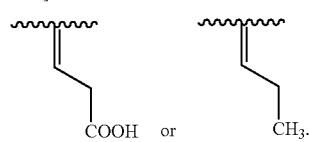

Also, $R^{2A}$ and $R^{2B}$ may be taken together to form optionally substituted hydroxyimino shown below:

[Chemical Formula 35]

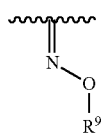

wherein $R^9$ is as defined above. Preferred is a group shown below.

[Chemical Formula 36]

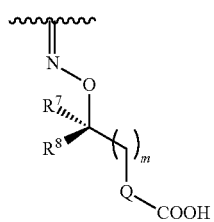

wherein $R^7$ and $R^8$ are each independently a hydrogen atom, halogen, hydroxyl group, carboxyl group, an optionally substituted lower alkyl group, an optionally substituted carbocyclic group, or an optionally substituted heterocyclic group, or
$R^7$ and $R^8$ may be taken together with a neighboring atom to form an optionally substituted carbocyclic group or an optionally substituted heterocyclic group;
Q is a single bond, an optionally substituted carbocyclic group or an optionally substituted heterocyclic group; and
m is an integer from 0 to 3.

Examples of "$R^7$ and $R^8$" includes hydrogen, fluoro, chloro, hydroxy, carboxy, methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, 3,4-dihydroxybenzyl, phenyl, 4-hydroxyphenyl, 3,4-dihydroxyphenyl, naphthyl, cyclopropyl, cyclobutyl, cyclopentyl, cyclohexyl, pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like.

Preferred combinations of ($R^7$, $R^8$) include (hydrogen, hydrogen), (methyl, hydrogen), (hydrogen, methyl), (methyl, methyl), (ethyl, hydrogen), (hydrogen, ethyl), (ethyl, ethyl), (phenyl, hydrogen), (hydrogen, phenyl), (dihydroxyphenyl, hydrogen), (hydrogen, dihydroxyphenyl), (carboxymethyl, hydrogen), (hydrogen carboxymethyl), (carboxyethyl, hydrogen), (hydrogen, carboxyethyl), (hydroxyethyl, hydrogen), (hydrogen, hydroxyethyl), (carbamoylmethyl, hydrogen), (hydrogen, carbamoylmethyl), (trifluoromethyl, hydrogen), (carboxy, hydrogen), (carbamoylethyl, hydrogen), (benzyl, hydrogen), (dihydroxybenzyl, hydrogen), and the like. More preferred combinations of ($R^7$, $R^8$) include, (methyl, methyl), (hydrogen, carboxymethyl), and (carboxyethyl, hydrogen).

Preferred examples of the above substituted hydroxyimino include groups shown bellow.

[Chemical Formula 37]

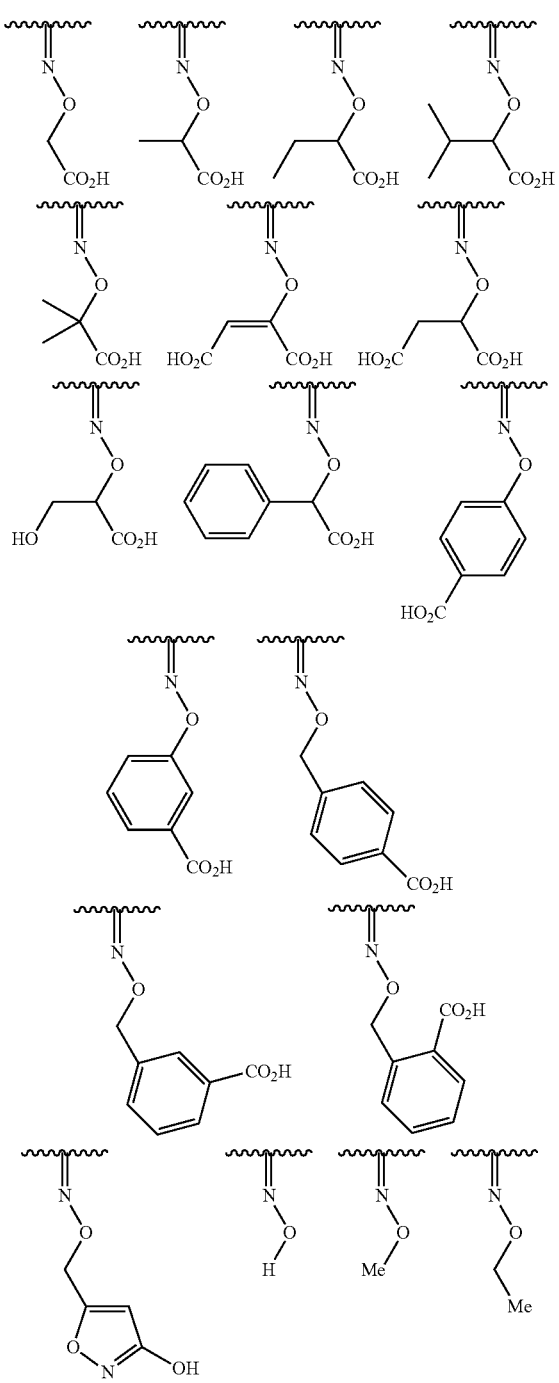

-continued

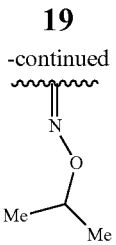

More preferred examples of the above substituted hydroxyimino include groups shown bellow.

[Chemical Formula 38]

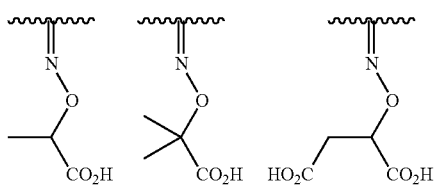

In the case where "$R^7$ and $R^8$ may be taken together with a neighboring atom to form an optionally substituted carbocyclic group or an optionally substituted heterocyclic group" in the formula:

[Chemical Formula 39]

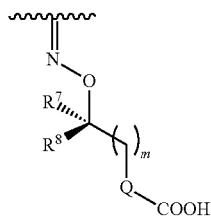

wherein each symbol is as defined, $R^7$ and $R^8$ may form cycloalkane, cycloalkene, or a non-aromatic heterocycle optionally substituted with a group selected from Substituent Group alpha.

For example, the moiety in the above formula:

[Chemical Formula 40]

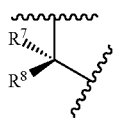

includes those shown below:

[Chemical Formula 41]

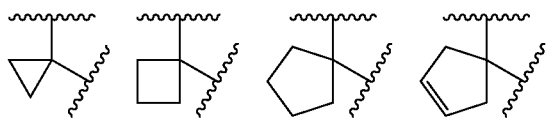

-continued

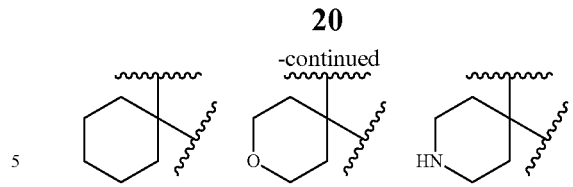

wherein each ring is optionally substituted with a group selected from Substituent Group alpha.

Examples of "Q" include a single bond, phenyl, pyridyl, and the like. A single bond is particularly preferable.

"m" is preferably 0 or 1, and 0 is particularly preferable.

Preferred examples of the above embodiments include:

[Chemical Formula 42]

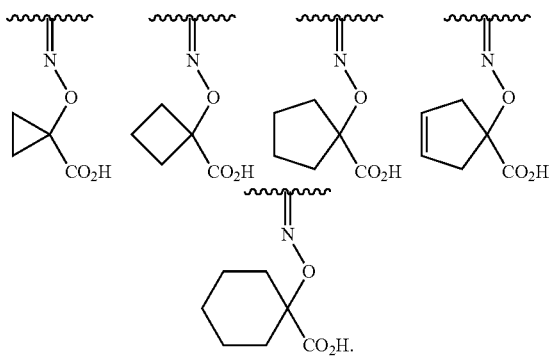

More preferred examples of $P^1$ include a group represented by the formula:

[Chemical Formula 43]

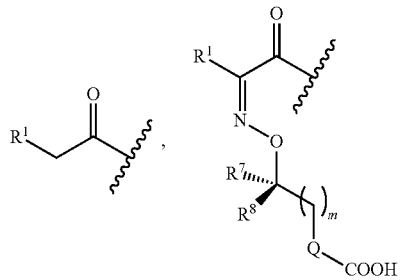

wherein, each symbol is as defined above.

The crystal of compound XVI-2, compound II-3, and compound III-2 may be identified by their main or characteristic peaks obtained by powder X-ray diffraction analysis. These crystals may be solvates such as hydrates or alcoholates. By isolating and using these crystals, the synthesis of 2-alkyl cephem can be conducted more efficiently.

When the crystal of the present invention is measured by powder X-ray diffraction analysis, measurement error may occur in peaks to some extent depending on a measurement apparatus or measurement conditions. Specifically, for example a measurement error of about ±0.2 may occur in value of 2θ. Even when a very high-precision equipment is used a measurement error of about ±0.1 may occur. Therefore, measurement error should be considered in identifying each crystal structure.

The crystals of the present invention have good stability, good handling, and/or high purity.

Scheme 1

[Chemical Formula 44]

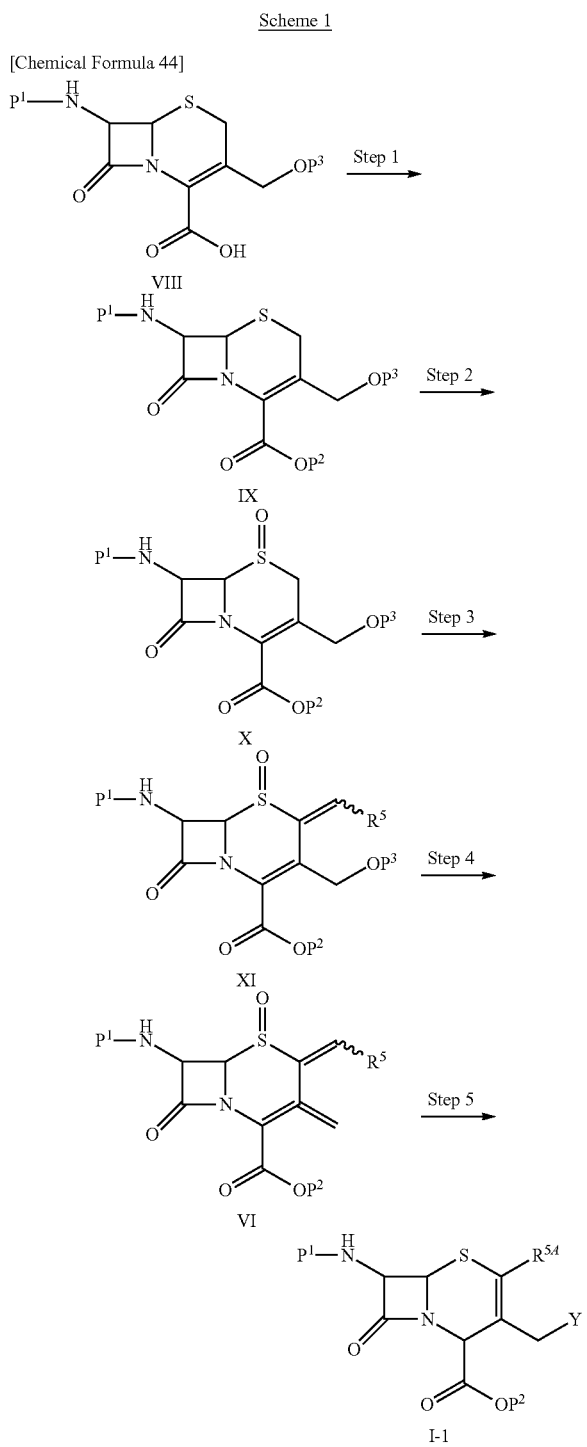

wherein, $P^1$ is an amino-protecting group; $P^2$ is a carboxy-protecting group; $P^3$ is a hydroxyl-protecting group; Y is a leaving group (e.g., a halogen (Cl, Br, I, F), acetoxy, substituted sulfonyloxy (e.g. methanesulfonyloxy, optionally substituted benzensulfonyloxy (benzenesulfonyloxy, p-toluenesulfonyloxy, etc.) trifluoromethanesulfonyloxy), and the like.); $R^5$ is hydrogen or lower alkyl; the other symbols are as defined above.

The process of the present invention is explained below.

Step 1

The 4-carboxyl group of the compound (VIII) is protected with a carboxyl-protecting group by a conventional method to give the compound (IX). The carboxyl-protecting group is exemplified by diphenyl methyl, p-methoxybenzyl etc.

The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water and a mixed solvent thereof.

The reaction temperature is usually in the range of from about −100° C. to 100° C., preferably from about −80° C. to 80° C., more preferably from about −60° C. to 60° C. The reaction time may vary according to the reagents, solvents or reaction temperature to be employed, but usually is 0.5 to 24 hours.

Examples of the amino-protecting group include phthalimide, acyl (formyl, optionally substituted alkylcarbonyl (chloroacetyl, trichloroacetyl etc.), lower alkoxycarbonyl (butoxycarbonyl (Boc), benzyloxy carbonyl etc.), lower alkenyloxycarbonyl (allyloxycarbonyl (Alloc), etc.), optionally substituted aralkyloxycarbonyl(benzyloxycarbonyl, p-nitrobenzyloxycarbonyl etc.), optionally substituted heteroaralkylcarbonyl (thienylmethylcarbonyl etc.)), optionally substituted aralkanoyl (p-nitrobenzoyl, etc.), optionally substituted aralkyl (trityl, benzhydryl (BH) etc.), optionally substituted arylimino (N-benzylidene, N-salicylidene, N-2-methoxybenzylidene etc.), optionally substituted lower alkylimino (N-isopropylidene etc.) tri-lower alkylsilyl (trimethylsilyl, tert-butyldimethylsilyl etc.) and the like. Preferably, the amino-protecting group is optionally substituted heteroaralkylcarbonyl (thienylmethylcarbonyl etc.), lower alkoxycarbonyl (butoxycarbonyl (Boc), benzyloxy carbonyl etc.), optionally substituted aralkyl (trityl, benzhydryl (BH) etc.), formyl, chloroacetyl, trichloroacetyl or tri-lower alkylsilyl (trimethylsilyl, tert-butyldimethylsilyl etc.), more preferably is optionally substituted heteroaralkylcarbonyl (thienylmethylcarbonyl etc.).

Examples of the hydroxy-protecting group include lower alkoxycarbonyl such as a C1-C4 alkoxycarbonyl (e.g., t-butyloxycarbonyl), halogenated lower alkoxycarbonyl such as a halogenated (C1-C3) alkoxycarbonyl (e.g., 2-iodo ethyloxycarbonyl, 2,2,2-trichloroethyloxycarbonyl), aryl-(lower) alkoxycarbonyl such as a phenyl-(C1-C4) alkoxycarbonyl having optionally a substituent(s) on the benzene ring (benzyloxycarbonyl, o-nitrobenzyloxycarbonyl, p-nitrobenzyloxycarbonyl, p-methoxybenzyloxycarbonyl), p-methoxybenzyl (PMB), tri-lower alkylsilyl such as tri-(C1-C4) alkylsilyl (e.g., trimethylsilyl, t-butyldimethylsilyl), a substituted methyl such as C1-C4 alkoxymethyl (e.g., methoxymethyl), C1-C4 alkoxy-(C1-C4) alkoxymethyl (e.g., 2-methoxyethoxymethyl), C1-C4 alkylthiomethyl (e.g., methylthiomethyl), tetrahydropyranyl, and the like.

Step 2

The compound (X) is obtained by subjecting the compound (IX) to oxidation reaction using an oxidant well-known to those skilled in the art (e.g., m-chloroperbenzoic acid, peracetic acid, performic acid, hydrogen peroxide).

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, water, and a mixed solvent selected from two or more of these solvents. Preferably halogenated hydrocarbons (e.g. dichloromethane, chloroform, carbon tetrachloride) are used as solvent.

The reaction temperature is usually in the range of from about −100° C. to 100° C., preferably from about −80° C. to 50° C., more preferably about −50° C. to 0° C.

The reaction time may vary according to the reagents, solvents or reaction temperature to be employed, but usually is carried out for 0.5 to 24 hours.

Step 3

The compound (X) is reacted with aldehyde (i.e., $R^5CHO$) and a primary or secondary amine to give the compound (XI).

The aldehyde includes, for example, formaldehyde and lower alkyl aldehyde (e.g. acetaldehyde, propionaldehyde). The aldehyde is generally used in an amount of about 1 to 100 mole, preferably 1 to 30 mole, for 1 mole of the compound (X).

The primary or secondary amine includes, for example, methylamine, dimethylamine, ethylamine and diethylamine. The primary or secondary amine, including its salt, is generally used in an amount of about 1 to 100 mole, preferably 1 to 30 mole, for 1 mole of the compound (X).

The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and a mixed solvent thereof.

The reaction temperature is usually in the range of from about −100° C. to 100° C., preferably from about −80° C. to 80° C., more preferably from about 0° C. to 80° C.

The reaction time may vary according to the reagents, solvents or reaction temperature to be employed, but usually is 0.5 to 24 hours.

Step 4

The compound (XI) is reacted with a reductant (e.g., zinc, copper, mixture thereof) and an acid (e.g., Hydrochloric acid, acetic acid, formic acid) to give the compound (VI).

Zinc is preferably used in an amount of about 1 to 100 mole, preferably 1 to 30 mole, for 1 mole of the compound (XI). The acid (e.g., Hydrochloric acid, acetic acid, formic acid) is preferably used in an amount of about 1 to 100 mole, preferably 1 to 30 mole, for 1 mole of the compound (XI).

The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), acid (e.g., Hydrochloric acid, acetic acid, formic acid), dimethylsulfoxide, water, and a mixed solvent thereof.

The reaction temperature is usually in the range of from about −100° C. to 100° C., preferably from about −80° C. to 80° C., more preferably from about −20° C. to 60° C.

The reaction time may vary according to the reagents, solvents or reaction temperature to be employed, but usually is 0.5 to 24 hours.

Step 5

The compound (VI) is reacted with an acid (e.g., hydrohalic acid, acetic acid, formic acid, methanesulfonic acid, torifluoromethanesulfonic acid, p-toluenesulfonic acid) to give the compound (I-1).

Preferably, the acid is hydrochloric acid or hydrobromic acid.

The acid is generally used in an amount of about 1 to 100 mole, preferably 1 to 30 mole, for 1 mole of the compound (VI).

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, water, and a mixed solvent selected from two or more of these solvents. Preferably, dioxane is used as solvent.

The reaction temperature is usually in the range of from about −100° C. to 100° C., preferably from about −10° C. to 50° C., more preferably from about −5° C. to 30° C.

The reaction time may vary according to the reagents, solvents or reaction temperature to be employed, but usually is 0.5 to 24 hours.

Scheme 2

[Chemical Formula 45]

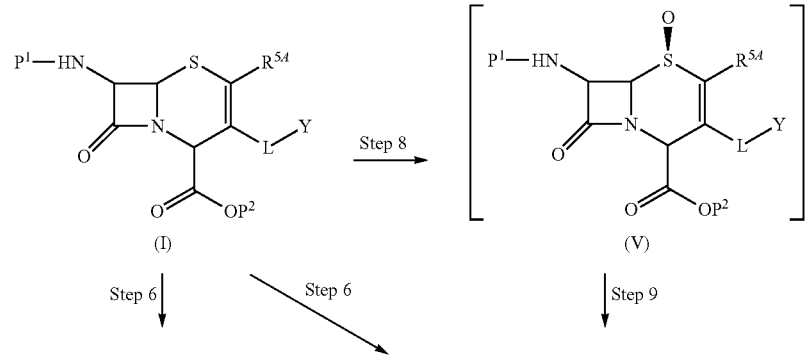

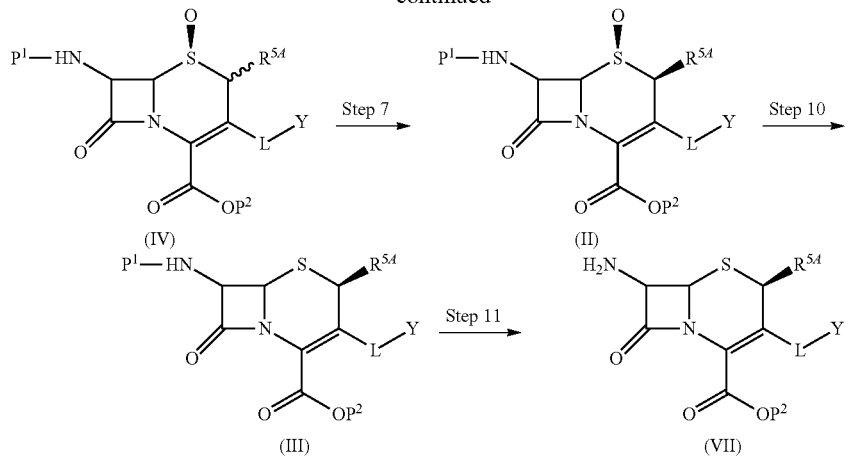

(IV)    (II)

(III)   (VII)

wherein each symbol is as defined above.

Step 6

The compound (I) is reacted with an oxidant well-known to those skilled in the art (e.g., m-chloroperbenzoic acid, peracetic acid, performic acid, hydrogen peroxide) to give (IV), which is a stereoisomeric mixture of sulfoxide compounds.

Preferably, the oxidant is m-chloroperbenzoic acid.

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, water, and a mixed solvent selected from two or more of these solvents. Preferably halogenated hydrocarbons (e.g. dichloromethane, chloroform, carbon tetrachloride) are used as solvent.

The reaction temperature is usually in the range of from about −100° C. to 100° C., preferably from about −80° C. to 50° C., more preferably about −60° C. to −20° C.

The reaction time may vary according to the reagents, solvents or reaction temperature to be employed, but usually is carried out for 0.5 to 24 hours.

In the above Scheme 2, the formula (IV):

[Chemical Formula 46]

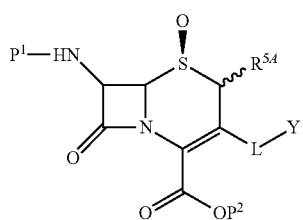

(IV)

includes the following structures:

[Chemical Formula 47]

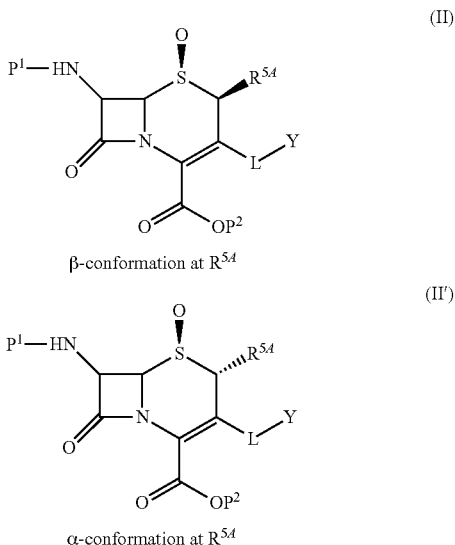

β-conformation at $R^{5A}$ (II)

α-conformation at $R^{5A}$ (II′)

or a mixture thereof.

Step 7

The stereoisomeric mixture of the sulfoxide compounds of the formula (IV) is reacted with a base (e.g. triethylamine, trimethylamine, dicyclohexylamine, ethanolamine, diethanolamine, meglumine, diisopropylethylamine, ethylenediamine, pyridine, pycoline, quinoline) to give the single stereoisomer sulfoxide compound (II) as major product. Through this reaction, 2-α-alkyl cephem compound can be transformed to 2-β-alkyl cephem compound (II).

Preferably, the base is triethylamine or diisopropylethylamine.

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, water, and a mixed solvent selected from two or more of these solvents. Preferably, Acetone, MeCN, EtOAc, THF, Dioxane, MeOH, $CH_2Cl_2$, $CHCl_3$, or EtOH is used as solvent. More preferably, Acetone is used as a solvent.

The reaction temperature is usually in the range of from about −100° C. to 100° C., preferably from about −80° C. to 50° C., more preferably about 0° C. to 30° C.

The reaction time may vary according to the reagents, solvents or reaction temperature to be employed, but usually is carried out for 0.5 to 24 hours.

More preferably, the obtained compound (II) can be purified by, for example, column chromatography, to give compound (II) in more high purity.

Step 8

The compound (I) is reacted with an oxidant to give the sulfoxide compound (V) as a major product. The compound (V) can, once isolated or not, be used in the next step 9.

The oxidant is preferably peroxyacid (e.g., meta-chloro peroxybenzoic acid, peroxyacetic acid, performic acid, hydrogen peroxide, tert-butyl hydroperoxide), more preferably peroxiacid which can be washed out with water in the postreaction treatment (e.g. peroxyacetic acid, performic acid, hydrogen peroxide, tert-butyl hydroperoxide). The oxidant is generally used in an amount of about 1 to 100 mole, preferably 1 to 30 mole, for 1 mole of Compound (I). The reaction solvents include, for example, alcohols (e.g., methanol, ethanol), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone). Preferably, halogenated hydrocarbons (e.g. dichloromethane, chloroform, carbon tetrachloride) is used as solvent.

The reaction temperature is usually in the range of from about −100° C. to 100° C., preferably from about −20° C. to 20° C., more preferably from about −10° C. to 10° C.

The reaction time may vary according to the reagents, solvents or reaction temperature to be employed, but usually is 0.5 to 24 hours.

The quench and postreaction treatment may be carried our by a conventional method of the oxidation reaction, where the solvent for washing is preferably water or brine.

Step 9

The compound (V) obtained by Step 8 is reacted with a base (e.g. triethylamine, sodium acetate, trimethylamine, diisopropylethylamine, dicyclohexylamine, ethanol amine, ethylenediamine, pyridine, picoline, quinoline, sodium carbonate, sodium hydrogen carbonate) to give the single stereoisomer sulfoxide compound (II). Preferably, the base is sodium acetate, sodium hydrogen carbonate or sodium carbonate, more preferably the base is sodium acetate.

The reaction solvents include, for example, water, alcohols (e.g., methanol, ethanol), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), nitriles (e.g., acetonitrile, propionitrile) or a mixture thereof. Preferably, the reaction solvent is a mixture of acetonitrile and water.

The reaction temperature is usually in the range of from about −100° C. to 100° C., preferably from about −50° C. to 50° C., more preferably from about 0° C. to 40° C.

The reaction time may vary according to the reagents, solvents or reaction temperature to be employed, but usually is 0.5 to 24 hours. Preferably, the reaction is performed at 20° C. to 40° C. for 0.5 to 4 hour, then cooled to 0° C. to 10° C. for 18 to 24 hours. The reaction pH is preferably from 5 to 8.

Step 10

The compound (II) is reacted with a reductant (e.g., phosphorus trichloride, phosphorus tribromide) to give the compound (III).

The reductant (e.g., phosphorus trichloride, phosphorus tribromide) is generally used in an amount of about 1 to 100 mole, preferably 1 to 30 mole, for 1 mole of Compound (II).

The reaction solvents include, for example, halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone).

The reaction temperature is usually in the range of from about −100° C. to 100° C., preferably from about −80° C. to 50° C., more preferably from about −60° C. to 0° C.

The reaction time may vary according to the reagents, solvents or reaction temperature to be employed, but usually is 0.5 to 24 hours.

Step 11

The compound (VII) is obtained by subjecting Compound (III) to deprotection of 7-amino-protecting group ($P^1$) by a conventional method described in Protective Groups in Organic Synthesis, written by T. W. Greene, John Wiley & Sons Inc. (1991) etc. For example, a hydrolysis reaction to make amide on 7-side chain to an amino group, followed by treating the compound with a hydrohalic acid such as hydrochloric acid. The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, water, and a mixed solvent selected from two or more thereof.

The reaction temperature is usually in the range of from about −100° C. to 100° C., preferably from about −50° C. to 50° C., more preferably from about −40° C. to 30° C.

The reaction time may vary according to the reagents, solvents or reaction temperature to be employed, but usually is 0.5 to 24 hours.

Scheme 3

[Chemical Formula 48]

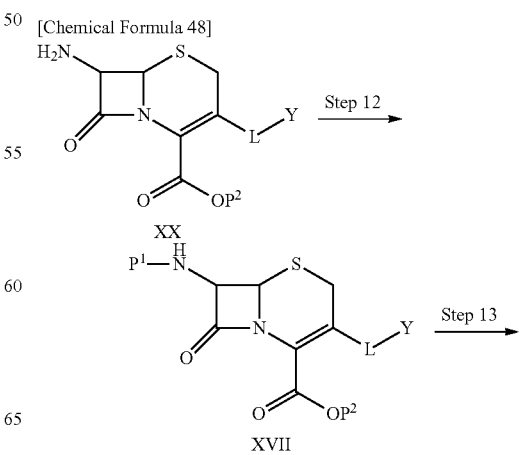

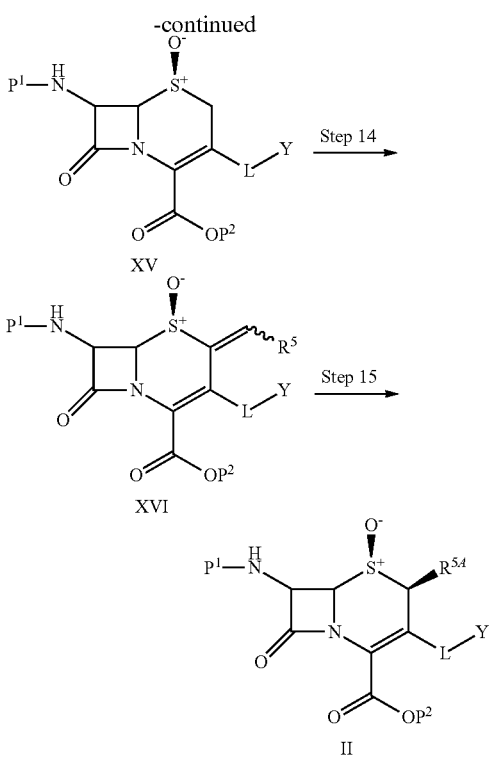

wherein, P¹ is acyl or an amino-protecting group; P² is a carboxy-protecting group; L is a single bond, lower alkylene or lower alkenylene; Y is a leaving group (e.g., halogen (Cl, Br, I, F), acetoxy, substituted sulfonyloxy (e.g., methanesulfonyloxy, optionally substituted benzensulfonyloxy (e.g. benzenesulfonyloxy, p-toluenesulfonyloxy), trifluoromethanesulfonyloxy), and the like.); R⁵ is hydrogen or lower alkyl; the other symbols are as defined above.

Step 12

The 7-amino group of the compound (XX) or a salt thereof is acylated with an acylating reagent or protected with an amino-protecting group by a conventional method to give the compound (XVII). The amino-protecting group is exemplified by benzoyl, phenoxy methyl carbonyl, thienyl methyl carbonyl etc.

The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water and a mixed solvent thereof.

The reaction temperature is usually in the range of about −100° C. to 100° C., preferably about −80° C. to 80° C., more preferably about −60° C. to 60° C. The reaction time may vary according to the reagents, solvents or reaction temperature to be employed, but usually is 0.5 to 24 hours.

Examples of the amino-protecting group include phthalimide, acyl (e.g., formyl, optionally substituted alkylcarbonyl (e.g., chloroacetyl, trichloroacetyl), lower alkoxycarbonyl (e.g., butoxycarbonyl (:Boc), benzyloxy carbonyl), lower alkenyloxycarbonyl (e.g., allyloxycarbonyl (:Alloc)), optionally substituted aralkyloxycarbonyl(e.g., benzyloxycarbonyl, p-nitrobenzyloxycarbonyl), optionally substituted heteroaralkylcarbonyl (e.g., thienylmethylcarbonyl)), optionally substituted aralkanoyl (e.g., p-nitrobenzoyl), optionally substituted aralkyl (e.g., trityl, benzhydryl (:BH)), optionally substituted arylimino (e.g., N-benzylidene, N-salicylidene, N-2-methoxybenzylidene etc.), optionally substituted lower alkylimino (e.g., N-isopropylidene) tri-lower alkylsilyl (e.g., trimethylsilyl, tert-butyldimethylsilyl) and the like. Preferably, the amino-protecting group is optionally substituted heteroaralkylcarbonyl (e.g., thienyl-methylcarbonyl), lower alkoxycarbonyl (e.g., butoxycarbonyl (:Boc), benzyloxy carbonyl), optionally substituted aralkyl (e.g., trityl, benzhydryl (:BH)), formyl, chloroacetyl, trichloroacetyl or tri-lower alkylsilyl (e.g., trimethylsilyl, tert-butyldimethylsilyl), more preferably is optionally substituted heteroaralkylcarbonyl (e.g., thienylmethylcarbonyl).

Examples of the carboxy protecting groups include lower alkyl (e.g., methyl, ethyl, t-butyl), (lower)alkylcarbonyloxymethyl (e.g., pivaloyl), optionally substituted aralkyl (e.g., benzyl, benzhydryl, phenethyl, p-methoxybenzyl, p-nitrobenzyl), silyl groups (t-butyldimethylsilyl, diphenyl (t-butyl)silyl), and the like.

Step 13

The compound (XV) is obtained by subjecting the compound (XVII) to oxidation reaction using an oxidant well-known to those skilled in the art (e.g., m-chloroperbenzoic acid, peracetic acid, performic acid, hydrogen peroxide).

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, water, and a mixed solvent selected from two or more of these solvents. Preferably halogenated hydrocarbons (e.g. dichloromethane, chloroform, carbon tetrachloride) are used.

The reaction temperature is usually in the range of about −100° C. to 100° C., preferably about −80° C. to 50° C., more preferably about −50° C. to 0° C.

The reaction time may vary according to the reagents, solvents or reaction temperature to be employed, and is usually 0.5 to 24 hours.

Step 14

The compound (XVI) is obtained by reacting aldehyde, amine, and the compound (XV). The reaction is preferably conducted in the presence of an acid.

The aldehyde is usually represented by the formula: $R^5C(=O)H$, wherein, $R^5$ is hydrogen or lower alkyl.

The aldehyde includes aldehyde equivalent such as self-polymer (e.g., paraformaldehyde, paraldehyde, trioxane), hydrate, hemiacetal, acetal and the like.

The amine include primary amine, secondary amine, tertiary amine, amino acid and a salt thereof (e.g., hydrochloride salt, sulfate salt), preferred is secondary amine (e.g., dimethylamine, diisopropylamine, N-methyl-p-anisidine, morpholine, pyrrolidine) or amino acid (e.g., L-proline, D-proline, N-methylglycine).

Imine which is obtained by reacting the aldehyde and the amine may be used as an alternative for the aldehyde and the amine.

The acid includes acetic acid, trifuluoiroacetic acid formic acid, methanesulfonic acid, trifluoromethanesulfonic acid, p-toluenesulfonic acid.

The acid is generally used in an amount of about 0.5 to 100 mole, preferably 1 to 20 mole for 1 mole of the compound (XV).

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), nitriles (e.g., MeCN, propionitrile), nitros (e.g., nitromethane, nitorethane, nitrobenzene), dimethylsulfoxide, water, and a mixed solvent selected from two or more of these solvents. Preferably halogenated hydrocarbons (e.g. dichloromethane, chloroform, carbon tetrachloride), amides (e.g., formamide, N,N-dimethylformamide, N,N-dimethylacetamide, N-methylpyrrolidone) or ethers (e.g., anisole, dioxane, tetrahydrofuran, diethyl ether, tert-butyl methyl ether, diisopropyl ether) are used.

The reaction temperature is usually in the range from about −100° C. to 100° C., preferably from about −80° C. to 80° C., more preferably about −20° C. to 70° C.

The reaction time may vary according to the reagents, solvents or reaction temperature to be employed, but usually is 0.5 to 24 hours.

Step 15

The compound (XVI) is reacted with a reductant (e.g. borane-ether complex, sodium borohydrate, sodium triacetoxyborohydrate, lithium aluminium hydride, diisobuthylalminiumu hydride) to give the compound (II).

Preferred example of the reductant is sodium borohydrate or borane-THF complex. The reductant is preferably used in an amount of about 0.1 to 10 mole, preferably 0.2 to 5 mole, for 1 mole of the compound (XVI).

The reaction solvents include, for example, alcohols (e.g., methanol, ethanol, isopropanol), ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), acid (e.g., Hydrochloric acid, alkylcarboxylic acid (e.g., acetic acid, propionic acid), formic acid, trifluoroacetic acid, hydroxy acid (e.g., citric acid, tartaric acid), dicarboxylic acid (e.g., oxalic acid, maleic acid), sulfonic acid (e.g., benzenesulfonic acid, p-toluenesulfonic acid)), dimethylsulfoxide, water, and a mixed solvent thereof.

The reaction temperature is usually in the range of about −100° C. to 100° C., preferably about −80° C. to 50° C., more preferably about −80° C. to 0° C.

The compound (II) may be obtained by hydrogenation reaction of the compound (XVI) with a metallic catalyst under $H_2$ gas.

The metallic catalyst includes rhodium metal, palladium on carbon, platinum oxide and the like.

The reaction solvents include, for example, alcohols (e.g., methanol, ethanol, isopropanol), ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), acid (e.g., Hydrochloric acid, acetic acid, formic acid), dimethylsulfoxide, water, and a mixed solvent thereof.

The reaction time may vary according to the reagents, solvents or reaction temperature to be employed, but usually is 0.5 to 24 hours.

The protecting group to be used in the above reactions such as amino-protecting groups, hydroxy-protecting groups, etc. includes, for example, protecting groups described in Protective Groups in Organic Synthesis, written by T. W. Greene, John Wiley & Sons Inc. (1991), etc. Methods for the introduction and removal of a protecting group are methods commonly used in synthetic organic chemistry (see, for example, methods described in Protective Groups in Organic Synthesis, written by T. W. Greene, John Wiley & Sons Inc. (1991)), etc. Furthermore, a functional group included in each substituent can be converted by a known method (e.g., those described in Comprehensive Organic Transformations, written by R. C. Larock (1989), etc.) in addition to the above production methods. Some of the compounds of the present invention can be used as a synthetic intermediate, leading to a new derivative. Intermediates and desired compounds produced in each of the above production methods can be isolated and purified by a purification method commonly used in the synthetic organic chemistry, for example, neutralization, filtration, extraction, washing, drying, concentration, recrystallization, any kind of chromatography, etc. Furthermore, intermediates can be subjected to a next reaction without any purification.

The above-mentioned deprotecting reaction is carried out in a solvent such as tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, or a mixed solvent thereof, using a Lewis acid (e.g., $AlCl_3$, $SnCl_4$, $TiCl_4$), a protonic acid (e.g., HCl, HBr, $H_2SO_4$, HCOOH), and the like.

The obtained compound may further be chemically modified to give various cephem compounds, including 4-carboxylic acid, ester thereof, 7-acyl type compound, cephem compound having a quaternary ammonium group at the 3-methyl side chain, pharmaceutically acceptable salt, or a solvate thereof.

Unless otherwise noted, all starting materials were obtained from commercial suppliers or synthesized by well known methods in the art. Unless otherwise indicated, temperature is expressed as ° C. (degrees Centigrade). Unless otherwise indicated, all reactions were conducted at ambient temperature.

All solvents are highest available purity and all reactions run under anhydrous conditions in an argon (Ar) or nitrogen ($N_2$) atmosphere where necessary.

$^1$H NMR (hereinafter also "NMR") spectra were recorded on Brucker AVANCE-400 spectrometers. $CDCl_3$ is deuteriochloroform, d6-DMSO is hexadeuteriodimethylsulfoxide, $D_2O$ is Deuterium oxide, and $CD_3OD$ is tetradeuteriomethanol. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (muitiplet), br (broad).

Mass spectra were run on Waters Open Architecture System, UPLC SQD MS analytical system. The compound was analyzed using a reverse phase column, e.g., Xbridge-C18, Sunfire-C18, Thermo Aquasil/Aquasil C18, Acquity HPLC C18, Acquity UPLC BEH C18, Shim-pack XR-ODS, Thermo Hypersil Gold eluted using an acetonitrile and water gradient with a low percentage of an acid modifier such as 0.1% formic acid.

Analytical HPLC was run using an Shimadzu system (10A-VP series or 20A series) with variable wavelength UV detection using COSMOSIL packed column (5018-AR-II) and eluting with an acetonitrile/water gradient containing a 0.05% or 0.1% TFA modifier (added to each solvent).

The condition for powder X-ray diffraction measurement is CuKa ray, 1.54 Angstroms (monochromator), tube voltage 30 kV, tube current 10 mA.

Unless otherwise indicated, flash chromatography was run on a Teledyne Isco Combiflash RF using disposable Redi-Sep flash columns (normal or reverse stationary phase as indicated), and a detector with UV wavelength at 254 nm. A styrenic adsorbent resin, DIAION™ HP20SS, was used in the workup and purification of cephalosporin analogs, and is referred to simply as HP20SS resin in the following examples.

EXAMPLES

Hereinafter, the present invention is described in more detail, however, the present invention is not construed to be limited thereto.

The meaning of each abbreviation is as described below.
Ac: Acetyl
Allooc: Allyloxycarbonyl
BH: Benzhydryl
Boc: tert-Butoxycarbonyl
Bn: Benzyl
DCM: dichloromethane
DMF: N,N-dimethylformamide
EDC: 1-ethyl-3-(3-dimethylaminopropyl)carbodiimide
Et: Ethyl
EtOAc: ethyl acetate
Eq.: mol equivalent
i-Pr: isopropyl
mCPBA: m-chloroperoxybenzoic acid
Me: methyl
Ms: methanesulfonyl
ODS: Octadecylsilyl
PMB: para-Methoxybenzyl
Py: pyridine
r.t.: room temperature
TBS: tert-butyldimethylsilyl
t-Bu: tert-butyl
tem: temperature
TFA: trifluoroacetic acid
V: volume (ml) of solvent per weight (g) of starting material

Example 1

Synthesis of Compound VII-1

[Chemical Formula 49]

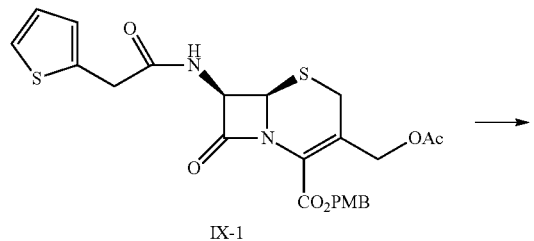

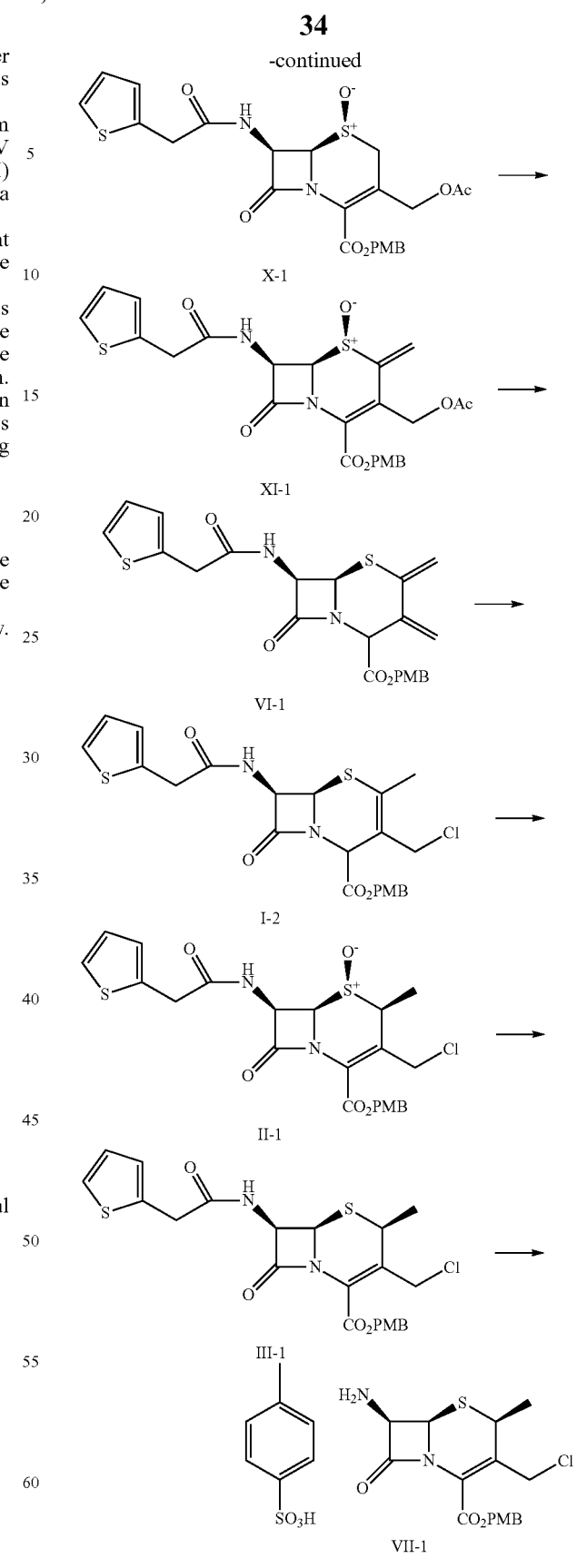

(1) Compound IX-1→Compound X-1→Compound XI-1

To a pre-cooled solution of compound IX-1 (50 g, 97 mmol), synthesized according to the synthesis in Tetrahedron Letter, 37, 1971-1974 (1996), in dichloromethane (450 mL) at −10° C. was added peracetic acid (19.82 g, 102 mmol, 37% Wt). The mixture was stirred at −10 to −5° C. To the resulting mixture was added a solution of sodium bisulfite (12.1 g, 116 mmol) in water (200 mL). Water (150 mL) was added to the mixture, and then an organic layer was separated. The organic layer was washed with water (250 mL), 10% aqueous solution of sodium chloride (250 mL). The aqueous layers were successively extracted with dichloromethane (150 mL). The combined organic layers were dried over magnesium sulfate and filtered. To the filtrated was added dimethylformamide (200 mL) and then the solution was concentrated to give crude compound (X-1), which was placed in a reaction bottle with dimethylformamide (30 mL) and then to the solution was added formaldehyde (15.7 g, 194 mmol, 37% Wt) and dimethylamine hydrochloride (7.89 g, 97 mmol). The mixture was stirred at 60° C. for 3 hours and then cooled in ice bath. To the mixture was added water (250 mL) dropwise over 8 minutes. The resulting mixture was stirred for 3.5 hr. The precipitated material was collected by filtration and washed with water (250 mL) and ethanol (250 mL). The solid was dried under air for 3 days to afford compound XI-1 (48.5 g, 92%).

$^1$H-NMR (DMSO-$D_6$) δ: 8.61 (1H, d, J=8.3 Hz), 7.39-7.35 (3H, m), 6.98-6.93 (4H, m), 6.40 (1H, s), 6.21 (1H, s), 5.95 (1H, dd, J=8.3, 5.1 Hz), 5.31-5.26 (2H, m), 5.21 (1H, d, J=11.9 Hz), 5.07 (1H, d, J=5.1 Hz), 4.74 (1H, d, J=12.5 Hz), 3.91 (1H, d, J=15.4 Hz), 3.83 (1H, d, J=15.4 Hz), 3.75 (3H, s), 1.96 (3H, s).

(2) Compound XI-1→Compound VI-1→Compound I-2

To a pre-cooled suspension of compound XI-1 (25.0 g, 45.9 mmol) in 1,4-dioxane (175 mL) and dichloromethane (50 mL) in ice bath was added zinc (15.01 g, 230 mmol) with dichloromethane (15 mL). To the mixture in ice bath was added concentrated hydrochloric acid (19.1 mL, 230 mmol, 12 M) dropwise over 45 minutes and then washed with dichloromethane (10 mL). The mixture was stirred in ice bath for 1 hour, and then filtered through Celite and washed with dichloromethane (300 mL). The filtrate was washed with water (500 mL) and water (125 mL) successively. The aqueous layers were successively extracted with dichloromethane (75 mL). The combined organic layers were dried over magnesium sulfate, filtered and concentrated to give crude compound VI-1, which was dissolved with 1,4-dioxane (75 mL) to remove dichloromethane and then cooled in ice bath. To the mixture was added hydrochloric acid in 1,4-dioxane (23.0 mL, 4M) and then stirred in ice bath for 2 hr. To the resulting mixture was added isopropyl ether (122 mL) and stirred in ice bath for 1.5 hr. The precipitated material was collected by filtration and washed with isopropyl ether. The solid was dried under air over night to afford compound I-2 (15.3 g, 58%). $^1$H-NMR (DMSO-$D_6$) δ: 9.27 (1H, d, J=7.8 Hz), 7.38-7.34 (3H, m), 6.97-6.92 (4H, m), 5.48 (1H, dd, J=7.8, 3.8 Hz), 5.19 (1H, d, J=3.8 Hz), 5.15-5.08 (3H, m), 4.64 (1H, d, J=12.2 Hz), 4.31 (1H, d, J=12.2 Hz), 3.77-3.74 (5H, m), 2.04 (3H, s).

(3) Compound I-2→Compound II-1

To a pre-cooled suspension of compound I-2 (50.0 g, 94 mmol) in dichloromethane (500 mL) in ice bath was added peracetic acid (18.4 g, 94 mmol, 39% Wt) dropwise over 10 minutes. The mixture was stirred in ice bath for 3 hours. An aqueous solution of sodium bisulfite (11.8 g, 113 mmol) in water (250 mL) was added. Water (250 mL) was further added. The organic layer was washed with water (500 mL) and 10% aqueous solution of sodium chloride (500 mL). The aqueous layers were successively extracted with dichloromethane (50 mL). The combined organic layers were concentrated while replaced a solvent to acetonitrile by adding twice (250 mL, 100 mL). To the residual suspension (approx. 250 mL) was added acetonitrile (612 mL) and water (150 mL). To the mixture was added 10% aqueous solution of sodium acetate (100 mL) and then pH showed 6.29. The mixture was stirred at room temperature with monitoring pH for 1.5 hours. 2 mol/L hydrochloric acid (24.5 mL) was added to quench. The insoluble material was collected by filtration and washed with water (200 mL) and acetonitrile (150 mL). The solid was dried under air over 3 days to afford compound II-1 (32.6 g, 66%).

$^1$H-NMR (DMSO-$D_6$) δ: 8.53 (1H, d, J 8.3 Hz), 7.38-7.36 (3H, m), 6.97-6.93 (4H, m), 5.88 (1H, dd, J=8.3, 4.9 Hz), 5.30 (1H, d, J=12.0 Hz), 5.21 (1H, d, J=12.0 Hz), 5.10 (1H, d, J=4.9 Hz), 4.81 (1H, d, J=12.3 Hz), 4.42 (1H, d, J=12.3 Hz), 3.90-3.79 (3H, m), 3.76 (3H, s), 1.61 (3H, d, J=7.5 Hz).

(4) Compound II-1→Compound III-1

To a pre-cooled suspension of compound II-1 (30.0 g, 57.4 mmol) in dimethylformamide (240 mL) with stirring at −40° C. was added phosphorus trichloride (23.6 g, 172 mmol) over 10 minutes. The mixture was stirred at −35° C. for 1 hour. To the resulting mixture was added dichloromethane (300 mL) and water (300 mL). The organic layer was separated, and then washed with water (300 mL) and 10% aqueous solution of sodium chloride (300 mL). The aqueous layers were successively extracted with dichloromethane (90 mL). The combined organic layers were dried over magnesium sulfate, filtered and concentrated to approx. 150 mL. To the residual suspension was added 2-propanol (180 mL) and then the suspension was concentrated to approx. 150 mL again. To the residue was added 2-propanol (14 mL) and diisopropyl ether (120 mL). The mixture was stirred for 3 hours. The insoluble material was collected by filtration and dried under air for 3 days to afford compound III-1 (20.8 g, 710).

$^1$H-NMR (DMSO-$D_6$) δ: 9.21 (1H, d, J=8.4 Hz), 7.38-7.34 (3H, m), 6.96-6.91 (4H, m), 5.73 (1H, dd, J=8.4, 5.0 Hz), 5.33 (1H, d, J=5.0 Hz), 5.27 (1H, d, J=11.9 Hz), 5.17 (1H, d, J=11.9 Hz), 4.66 (1H, d, J=12.0 Hz), 4.49 (1H, d, J=12.0 Hz), 4.08 (1H, q, J=7.2 Hz), 3.75 (5H, s), 1.53 (3H, d, J=7.2 Hz).

(5) Compound III-1→Compound VII-1

To a pre-cooled suspension of phosphorus pentachloride (8.21 g, 39.4 mmol) in dichloromethane (90 mL) with stirring at −5° C. was added pyridine (3.43 g, 43.4 mmol) and compound III-1 (10.0 g, 19.7 mmol). The mixture was stirred at 10 to 15° C. for 1 hour. The resulting mixture was poured into pre-cooled methanol (25 mL) in ice bath, and then water (50 mL) was added. The organic layer was separated and washed with water (100 mL). The aqueous layers were successively extracted with dichloromethane (40 mL). The combined organic layers were dried over magnesium sulfate, filtered. To the filtrate was added p-toluenesulfonic acid mono-hydrate (3.75 g, 19.7 mmol) and ethyl acetate (60 mL). The mixture was concentrated to remove dichloromethane. To the residual suspension was added ethyl acetate (50 mL). The mixture was stirred at 35° C., and then stirred in ice bath for 2.5 hours. The insoluble material was collected by filtration and washed with ethyl acetate. The solid was dried through air circulation to afford compound VII-1 (7.30 g, 63%).

$^1$H-NMR (DMSO-$D_6$) δ: 9.02 (3H, br s), 7.48 (2H, d, J=7.7 Hz), 7.36 (2H, d, J=8.3 Hz), 7.12 (2H, d, J=7.7 Hz), 6.94 (2H, d, J=8.3 Hz), 5.45 (1H, d, J=5.0 Hz), 5.29-5.17 (3H, m), 4.68 (1H, d, J=12.0 Hz), 4.51 (1H, d, J=12.0 Hz), 4.21 (1H, q, J=7.2 Hz), 3.75 (3H, s), 2.29 (3H, s), 1.57 (3H, d, J=7.2 Hz).

Example 2

Synthesis of Compound II-2

[Chemical Formula 50]

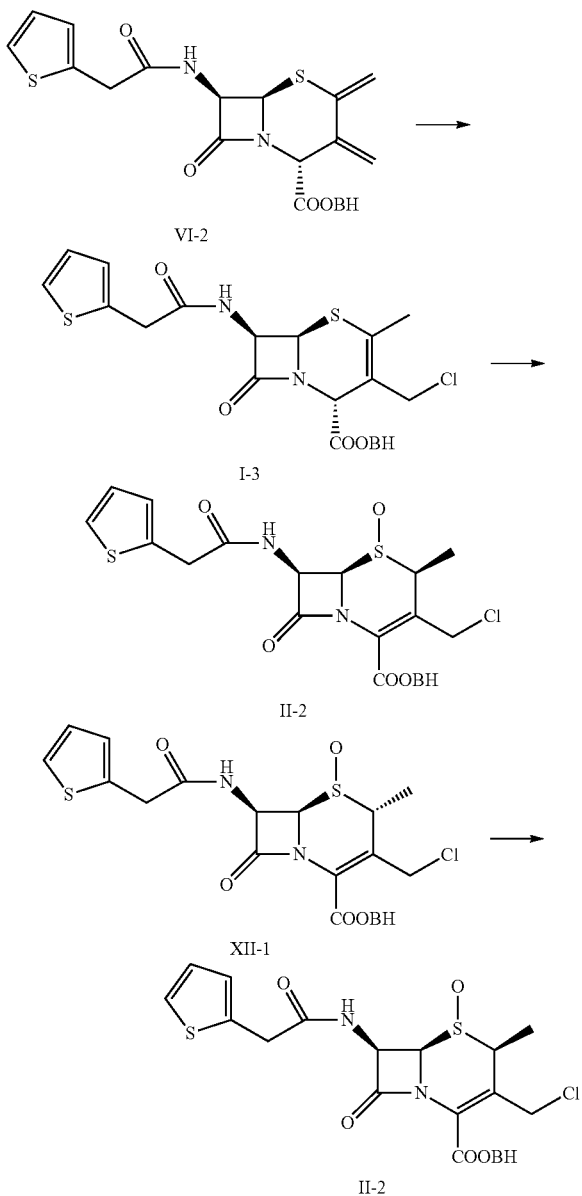

(1): Compound VI-2→Compound I-3

To a solution of compound VI-2 (26.47 g, 51.2 mmol) in 1,4-dioxane (200 mL) was added hydrochloric acid (4 mol/L in ethyl acetate, 25.6 mL, 102 mmol) at room temperature and then the mixture was stirred at same temperature for 1 hr. The solvent was removed by evaporation and to the residue was added dichloromethane and diisopropyl ether. The precipitated material was collected by filtration and dried under high vacuum to afford compound I-3 (21.11 g, 75%) as a solid.

$^1$H-NMR (CDCl3) δ: 1.99 (3H, s), 3.86 (2H, s), 4.09, 4.30 (2H, ABq, J=12.0 Hz), 5.20 (1H, s), 5.22 (1H, d, J=4.0 Hz), 5.61 (1H, dd, J=4.0 Hz, J=8.8 Hz), 6.36 (1H, d, J=8.8 Hz), 6.87 (1H, s), 7.00-7.02 (2H, m), 7.26-7.37 (11H, m).

(2) Compound VI-2→Compound I-3→Compound II-2, Compound XII-1

To a solution of compound VI-2 (94.58 g, 183 mmol) in 1,4-dioxane (800 mL) was added hydrochloric acid (4 mol/L in ethyl acetate, 92.1 mL, 366 mmol) at room temperature and then the mixture was stirred at same temperature for 1 hr. The solvent was removed by evaporation to give a crude containing compound I-3 as a foam. To a solution of the residual foam in dichloromethane (400 mL) with stirring at −50° C. was added a solution of mCPBA (63.2 g, 238 mmol) in dichloromethane (600 mL) over 40 min. The mixture was stirred at −50° C. for 1 hr. To the resulting mixture was added a solution of sodium bisulfite (23.9 g, 183 mmol) and sodium bicarbonate (10 g) in water (1000 mL). The organic layer was separated, washed with a solution of sodium bicarbonate twice, dried over magnesium sulfate, filtered and concentrated. The precipitated material was collected by "filtration" and dried under high vacuum to afford compound II-2 (18.51 g, 18%) as a solid.

$^1$H-NMR (CDCl3) δ: 1.61 (3H, d, J=7.6 Hz), 3.81-3.91 (3H, m), 4.39, 4.71 (2H, ABq, J=12.4 Hz), 5.16 (1H, d, J=3.2 Hz), 5.97 (1H, dd, J=5.2 Hz, J=8.0 Hz), 6.96-7.01 (3H, m), 7.30-7.51 (11H, m), 8.61 (1H, d, J=8.4 Hz).

The mother liquid after the above "filtration" was concentrated. The residue was purified by column chromatography on silica gel, eluted with ethyl acetate and n-hexane to afford a mixture of compound II-2 and compound XII-1 (ratio of 0.35 to 0.65) (34.2 g, 33% as a mixture).

$^1$H-NMR (CDCl3) δ: 1.27 (1.95H, d, J=7.6 Hz), 1.61 (1.05H, d, J=7.6 Hz), 3.81-4.04 (3H, m), 4.48, 4.52 (1.3H, ABq, J=11.6 Hz), 4.39, 4.71 (0.7H, ABq, J=12.4 Hz), 5.02 (0.65H, d, J=5.2 Hz), 5.16 (0.35H, d, J=3.2 Hz), 5.95-6.00 (1H, m), 6.96-7.01 (3H, m), 7.28-7.54 (11H, m), 8.51 (0.65H, d, J=8.8 Hz), 8.61 (0.35H, d, J=8.4 Hz).

(3) Isomerization of Compound XII-1 to Compound II-2

To a suspension of the mixture of compound II-2 and compound XII-1 (50 mg, ratio of 0.35 to 0.65, 0.088 mmol) in acetone (0.5 mL) with stirring in ice bath was added triethylamine (0.061 mL, 0.44 mmol). The mixture was stirred at room temperature for 1 hr. The insoluble material was collected by filtration after quenched by acetic acid (0.030 mL, 0.53 mmol). The collected solid was dried under high vacuum to afford a mixture of compound II-2 and compound XII-1 (30 mg, ratio of 8.8 to 1.0).

Example 3

Synthesis of Compound II-8

[Chemical Formula 51]

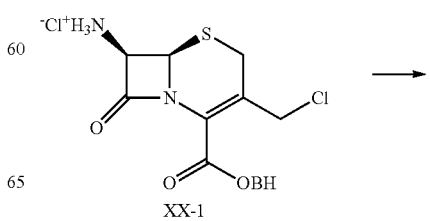

XX-1

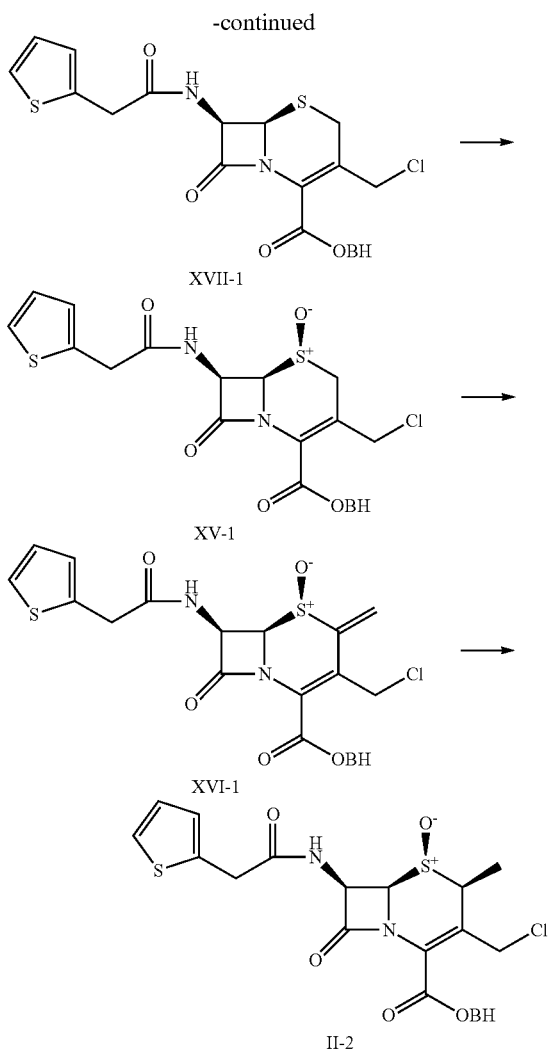

(1) Compound XX-1→Compound XVII-1

To a cooled (−10° C.) solution of thiophene-2-acetic acid (7.82 g, 55.0 mmol) in 250 mL of DMA was added triethylamine (7.62 ml, 55.0 mmol) followed by MsCl (4.29 ml, 55.0 mmol) in one portion. After 15 min, to this mixture was added compound XX-1 (22.6 g, 50.0 mmol) followed by triethylamine (7.62 mL, 55.0 mmol) at −10° C. After 1 hr the reaction mixture was poured into water then the aqueous layer was extracted with ethyl acetate. The combined extracts were washed with water and brine, dried (MgSO$_4$), filtered, and concentrated in vacuo. The residue was purified by flash chromatography to afford 18.0 g of compound XVII-1 (67%).

$^1$H-NMR (CDCl$_3$) δ: 7.43-7.22 (m, 11H), 7.04-6.94 (m, 3H), 6.31 (d, J=9.1 Hz, 1H), 5.87 (dd, J=9.1, 5.0 Hz, 1H), 4.98 (d, J=5.0 Hz, 1H), 4.37 (s, 2H), 3.86 (s, 2H), 3.60 (d, J=18.3 Hz, 1H), 3.45 (d, J=18.3 Hz, 1H).

(2) Compound XVII-1→Compound XV-1

To a cooled (−40° C.) solution of compound XVII-2 (17.9 g, 33.2 mmol) in dichloromethane was added 65% mCPBA (9.70 g, 36.5 mmol). After stirring for 30 min at −40° C., the mixture was quenched by 50 mL of 10% sodium bisulfite aqueous solution. The aqueous layer was extracted with dichloromethane and the combined extracts were washed with water and brine, dried (MgSO$_4$), filtered, and concentrated in vacuo. The resulting solid was washed with diisopropyl ether to afford 15.8 g of compound XV-1 (86%).

$^1$H-NMR (DMSO-D$_6$) δ: 8.52 (d, J=8.4 Hz, 1H), 7.54 (d, J=7.4 Hz, 2H), 7.44 (d, J=7.3 Hz, 2H), 7.39-7.27 (m, 7H), 6.98 (m, 3H), 5.96 (dd, J=8.4, 4.8 Hz, 1H), 5.00 (d, J=3.8 Hz, 1H), 4.62 (d, J=11.5 Hz, 1H), 4.47 (d, J=11.4 Hz, 1H), 3.98-3.72 (m, 4H).

(3) Compound XV-1→Compound XVI-1

To a slurry of L-Proline (1.24 g, 10.8 mmol) in dichloromethane (20 mL) was added acetic acid (1.03 ml, 18.0 mmol). To the resulting clear solution was added compound XV-1 (1.00 g, 1.80 mmol) followed by formaldehyde gas generated from paraformaldehyde (0.811 g, 27.0 mmol) by heating. After the mixture was stirred at r.t. for 2.5 hr, H$_2$O was added to the mixture then the organic solvent was removed by evaporation. The resulting solid was collected by filtration and washed with H$_2$O and MeOH to afford 819 mg of compound XVI-1 (80%)

$^1$H-NMR (DMSO-D$_6$) δ: 8.62 (d, J=8.3 Hz, 1H), 7.54 (d, J=7.3 Hz, 2H), 7.45 (d, J=7.4 Hz, 2H), 7.42-7.34 (m, 5H), 7.34-7.28 (m, 2H), 7.04 (s, 1H), 7.00-6.95 (m, 2H), 6.51 (d, J=1.3 Hz, 1H), 6.32 (d, J=1.3 Hz, 1H), 6.01 (dd, J=8.3, 5.0 Hz, 1H), 5.14 (d, J=5.0 Hz, 1H), 4.87 (d, J=11.9 Hz, 1H), 4.54 (d, J=11.9 Hz, 1H), 3.91 (d, J=15.4 Hz, 1H), 3.84 (d, J=15.4 Hz, 1H).

(4) Compound XVI-1→Compound II-2

To a cooled (−40° C.) solution of sodium borohydride (40.0 mg, 1.06 mmol) in MeOH (40 mL) was added dropwise a solution of compound XVI-1 (500 mg, 0.882 mmol) in 30 ml of THF under −35° C. (compound XVI-1 was dissolved in THF at 60° C. then cooled to r.t.). After the mixture was stirred at −40° C. for 20 min, TFA (0.163 ml, 2.12 mmol) was added. After the solution was diluted with H$_2$O and EtOAc, the organic solvent was removed by evaporation. The resulting solid was collected by filtration and washed by H$_2$O, EtOAc and MeOH to afford 416 mg of compound II-2 (83%). The stereochemistry of C-2 position was confirmed by NOE experiment and the ratio of 2-α:2-β showed 23:1 by $^1$H NMR.

$^1$H-NMR (DMSO-D$_6$) δ: 8.60 (d, J=8.3 Hz, 1H), 7.49 (d, J=7.0 Hz, 2H), 7.44-7.28 (m, 9H), 7.02-6.93 (m, 3H), 5.96 (dd, J=8.3, 4.8 Hz, 1H), 5.16 (d, J=4.8 Hz, 1H), 4.70 (d, J=12.3 Hz, 1H), 4.38 (d, J=12.3 Hz, 1H), 3.92-3.81 (m, 3H), 1.61 (d, J=7.5 Hz, 3H).

Example 4

Synthesis of Compound XVI-1

[Chemical Formula 52]

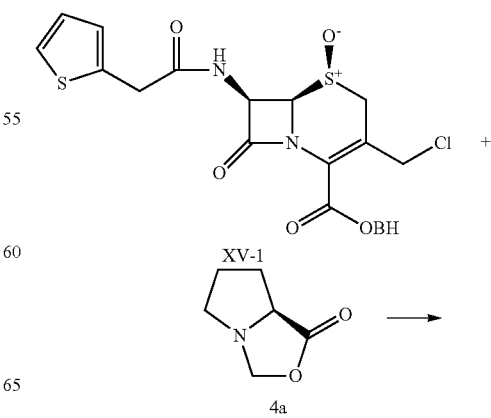

-continued

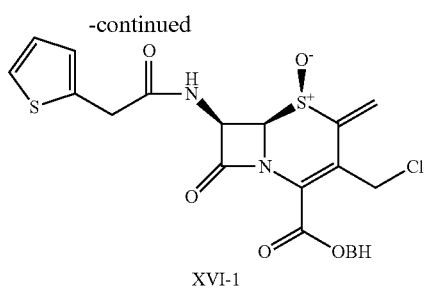

XVI-1

To a slurry of compound 4a (153 mg, 1.203 mmol; ref. *J. Org. Chem.* 2003, 68, 2652-2667) in dichloromethane (1 mL) was added compound XV-1 (100 mg, 0.18 mmol), acetic anhydride (0.238 ml, 2.52 mmol) and acetic acid (0.082 ml, 1.44 mmol). After the mixture was stirred at r.t. overnight, $H_2O$ was added to the mixture then the organic solvent was removed by evaporation. The resulting solid was collected by filtration and washed by $H_2O$ and MeOH to afford 30.4 mg of compound XVI-1 (30%)

$^1$H-NMR (DMSO-D$_6$) δ: 8.62 (d, J=8.4 Hz, 1H), 7.55-7.29 (m, 12H), 7.03 (s, 1H), 7.01-6.94 (m, 2H), 6.51 (s, 1H), 6.32 (s, 1H), 6.01 (dd, J=8.4, 5.0 Hz, 1H), 5.14 (d, J=5.0 Hz, 1H), 4.87 (d, J=12.0 Hz, 1H), 4.54 (d, J=12.0 Hz, 1H), 3.91 (d, J=15.4 Hz, 1H), 3.84 (d, J=15.4 Hz, 1H).

Compound XVI-1 was also obtained by the following reaction conditions shown in Table 1.

[Chemical Formula 53]

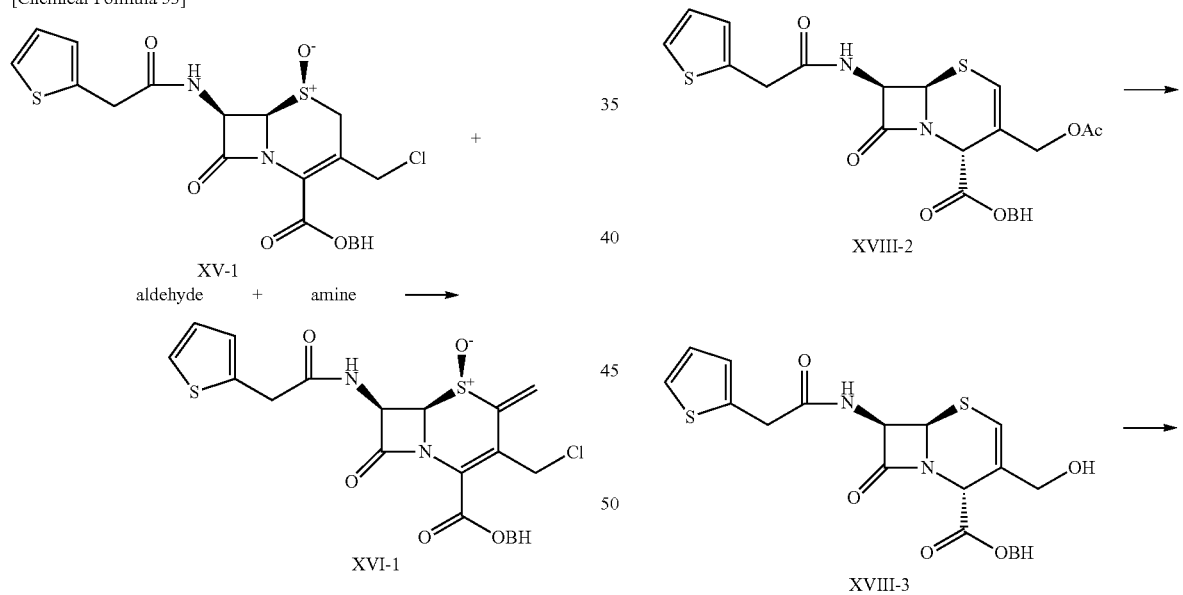

Example 5

Synthesis of Compound XV-1

[Chemical Formula 54]

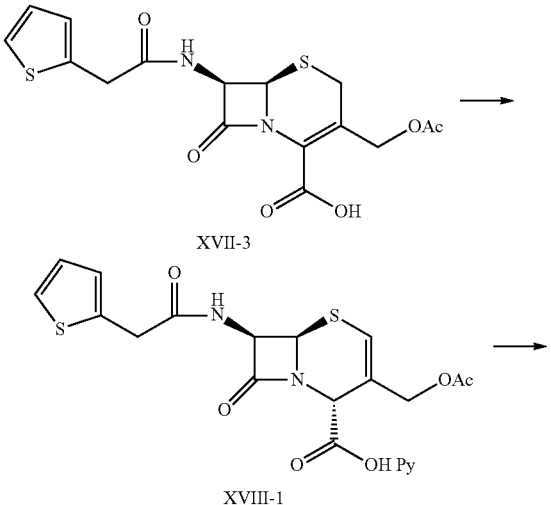

TABLE 1

| entry | amine (eq.) | aldehyde (eq.) | acid (eq.) | solvent | temp. (° C.) | yield of TM (%) |
|---|---|---|---|---|---|---|
| 1 | dimethylamine hydrochloride (1) | 36% formalin (2) | acetic acid (5) | DMF | 50 | 56 |
| 2 | N,N-deimethylmethyleneiminium chloride (1.1) | | | DMF | 65 | 40 |
| 3 | D-proline (1) | 36% formalin (2) | acetic acid (5) | DMF | 50 | 53 |
| 4 | N,N,N',N'-tetramethyldiaminomethane (5) | | acetic acid (8) | DCM | 0 | 63 |
| 5 | L-proline (6) | paraformaldehyde (15) | acetic acid (10) | DCM | 25 | 75 | eq.: mol equivalent to compound XV-1
temp.: temperature
yield of TM: yield of compound (XVI-1) by HPLC.

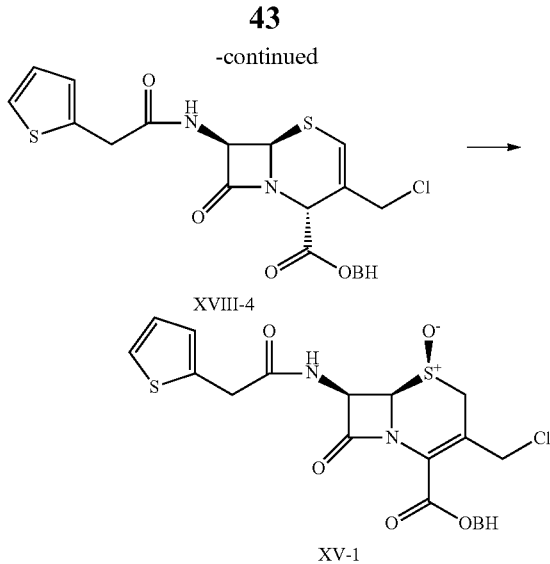

XVIII-4

XV-1

(1) Compound XVII-3→Compound XVIII-1

To a cooled (0° C.) solution of compound XVII-3 (39.6 g, 100 mmol) in pyridine (180 mL) was added acetic anhydride (18.9 ml, 200 mmol). After 4 hr, the resulting precipitate was collected by filtration and washed by EtOAc to afford 33.7 g of compound XVIII-1 (71%).

$^1$H-NMR (CDCl$_3$) δ: 8.65 (d, J=4.5 Hz, 2H), 7.88 (t, J 7.7 Hz, 1H), 7.52-7.45 (m, 2H), 7.29-7.25 (m, 3H), 7.03-6.98 (m, 2H), 6.40-6.33 (m, 2H), 5.68 (dd, J=9.0, 4.0 Hz, 1H), 5.36 (d, J=4.0 Hz, 1H), 5.02 (s, 1H), 4.83 (d, J=12.6 Hz, 1H), 4.69 (d, J=12.6 Hz, 1H), 3.87 (s, 2H), 2.08 (s, 3H).

(2) Compound XVIII-1→Compound XVIII-2

To a suspension of compound XVIII-1 (14.3 g, 30.0 mmol) in EtOAc (150 ml) was added 2 mmol/l aqueous hydrochloric acid solution (30.0 ml, 60.0 mmol) with stirring. After 5 min, the resulting mixture was separated and the organic layer was washed by brine, dried over MgSO$_4$, filtered, and evaporated in vacuo. The residue was dissolved in tetrahydrofuran (150 ml). Then to this solution was added dropwise a solution of diphenyl diazomethane (6.41 g, 33.0 mmol) in tetrahydrofuran at room temperature. When the reaction finished the mixture was concentrated in vacuo. The residue was added diisopropyl ether then resulting solid was collected by filtration and washed by diisopropyl ether to afford 16.6 g of compound XVIII-2 (99%). $^1$H-NMR (CDCl$_3$) δ: 7.39-7.27 (m, 1H), 7.02-6.98 (m, 2H), 6.88 (s, 1H), 6.39 (s, 1H), 6.31 (d, J=8.9 Hz, 1H), 5.63 (dd, J=8.9, 4.0 Hz, 1H), 5.19 (d, J=4.0 Hz, 1H), 5.10 (s, 1H), 4.55 (s, 2H), 3.85 (s, 2H), 1.94 (s, 3H), 1.55 (s, 3H).

(3) Compound XVIII-2→Compound XVIII-3

To a solution of compound XVIII-2 (5.00 g, 8.89 mmol) in tetrahydrofuran (150 ml) and water (50 ml) was added 10 mmol/l aqueous sulfuric acid solution (17.7 ml, 178 mmol) and stirred overnight. The mixture was poured into a mixture of water and ethyl acetate. The aqueous layer was extracted with ethyl acetate. The combined organic layers were washed with water and brine, dried over MgSO$_4$, filtered and concentrated in vacuo. The resulting solid was collected by filtration and washed with isopropyl acetate to afford 3.01 g of compound XVIII-3 (65.1%). The mother liquors was concentrated and chromatographed to provide second crop of compound XVIII-3 (354 mg, 7.6%). The total yield was 3.35 g (73%) of compound XVIII-3.

$^1$H-NMR (DMSO-D$_6$) δ: 9.20 (d, J=7.8 Hz, 1H), 7.46-7.33 (m, 9H), 7.33-7.27 (m, 3H), 6.99-6.90 (m, 2H), 6.84 (s, 1H), 6.50 (s, 1H), 5.46 (dd, J=7.7, 3.9 Hz, 1H), 5.20 (s, 1H), 5.16-5.11 (m, 2H), 3.97 (br s, 2H), 3.77 (s, 2H).

(4) Compound XVIII-3→Compound XVIII-4

To a cooled (−20° C.) slurry of phosphorus pentachloride (2.65 g, 12.7 mmol) in dichloromethane (30.0 ml) was added pyridine (1.03 ml, 12.7 mmol) followed by compound XVIII-3 (3.01 g, 5.78 mmol). After the mixture was stirred for 45 min at −20° C., the mixture was quenched with water. The aqueous layer was extracted with dichloromethane. The combined organic layers were washed with water and brine, dried over MgSO$_4$, filtered and concentrated in vacuo. The resulting solid was collected filtration and washed with isopropyl acetate to afford 1.11 g of compound XVIII-4 (36%). The mother liquors were concentrated and chromatographed to provide second crop of compound XVIII-4 (492 mg, 16%). The total yield was 1.6 g of XVIII-4 (51%).

$^1$H-NMR (DMSO-D$_6$) δ: 9.27 (d, J=7.8 Hz, 1H), 7.44-7.29 (m, 11H), 6.99-6.93 (m, 3H), 6.86 (s, 1H), 5.53 (dd, J=3.8, 7.8 Hz, 1H), 5.26 (s, 1H), 5.17 (d, J=3.8 Hz, 1H), 4.47 (d, J=11.7 Hz, 1H), 4.27 (d, J=11.7 Hz, 1H), 3.77 (s, 2H).

(5) Compound XVIII-4→Compound XV-1

To a cooled (−40° C.) solution of compound XVIII-4 (1.00 g, 1.86 mmol) in dichloromethane (10 ml) was added 65% mCPBA (0.591 g, 2.23 mmol). After stirring for 1 hr at −40° C., the mixture was quenched by 10% sodium bisulfite aqueous solution. The aqueous layer was extracted with dichloromethane and the combined extracts were washed with water and brine, dried (MgSO$_4$), filtered, and concentrated in vacuo. The residue was purified by silica gel chromatography to afford 798 mg g of compound XV-1 (78%).

$^1$H-NMR (DMSO-D$_6$) δ: 8.51 (d, J=8.3 Hz, 1H), 7.53 (d, J=7.6 Hz, 2H), 7.44 (d, J=7.6 Hz, 2H), 7.39-7.29 (m, 7H), 7.02-6.92 (m, 3H), 5.96 (dd, J=8.3, 4.7 Hz, 1H), 5.00 (d, J=4.7 Hz, 1H), 4.62 (d, J=11.4 Hz, 1H), 4.47 (d, J=11.4 Hz, 1H), 3.98-3.72 (m, 4H).

Example 6

Synthesis of Compound III-2

[Chemical Formula 55]

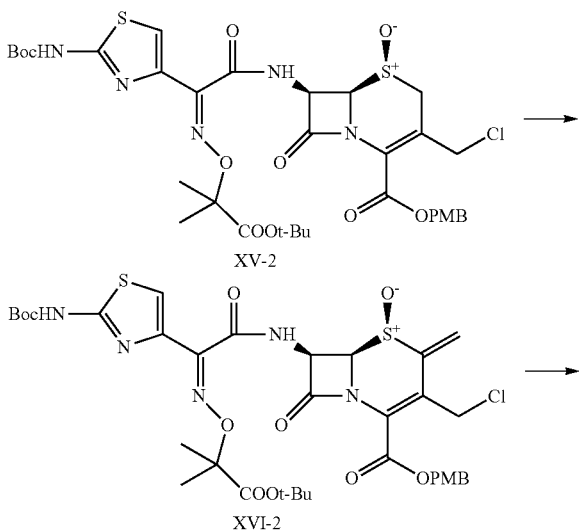

XV-2

XVI-2

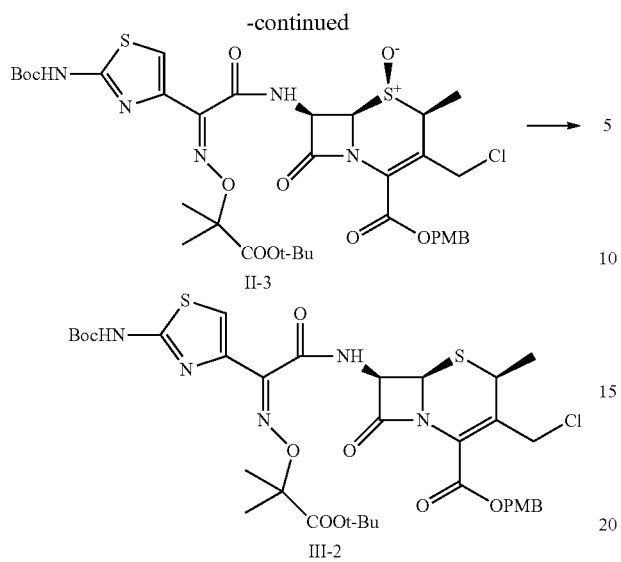

(1) Compound XV-2→Compound XVI-2

To a slurry of L-Proline (867 mg, 7.53 mmol) in dichloromethane (20 mL) was added acetic acid (0.718 ml, 12.6 mmol). To the resulting clear solution was added compound XV-2 (1.00 g, 1.26 mmol) followed by formaldehyde gas generated from paraformaldehyde (0.566 g, 18.8 mmol) by heating. After the mixture was stirred at r.t. overnight, H$_2$O was added to the mixture, then the organic solvent was removed by evaporation. The aqueous layer was extracted with ethyl acetate and the combined extracts were washed with water and brine, dried (MgSO$_4$), filtered, and concentrated in vacuo. The residue was purified by silica gel chromatography to afford 635 mg of compound XVI-2 (containing of 25% of compound XV-2).

$^1$H-NMR (CDCl$_3$) δ: 8.17 (br s, 1H), 7.95 (d, J=9.9 Hz, 1H), 7.37 (d, J=8.6 Hz, 2H), 7.29 (s, 1H), 6.93 (d, J=8.6 Hz, 2H), 6.45 (s, 1H), 6.24 (dd, J=9.9, 5.0 Hz, 1H), 5.37-5.23 (m, 3H), 4.72 (d, J=5.0 Hz, 1H), 4.25 (d, J=11.9 Hz, 1H), 3.83 (s, 3H), 1.61 (d, J=7.9 Hz, 6H), 1.54 (s, 9H), 1.40 (s, 9H).

(2) Compound XVI-2→Compound II-3

To a cooled (−40° C.) solution of sodium borohydride (35.7 mg, 0.943 mmol) in MeOH (9 mL) was added dropwise a solution of compound XVI-2 (635 mg, 0.786 mmol) in 6 ml of THF under −35° C. After the mixture was stirred at −40° C. for 15 min, TFA (0.145 ml, 1.89 mmol) was added. The solution was diluted with H$_2$O and EtOAc, the aqueous layer was extracted with ethyl acetate and the combined extracts were washed with water and brine, dried (MgSO$_4$), filtered, and concentrated in vacuo. The residue was purified by silica gel chromatography to afford 436 mg of compound II-3 (68% in 2 steps).

$^1$H-NMR (CDCl$_3$) δ: 8.38 (br s, 1H), 8.08 (d, J=9.9 Hz, 1H), 7.35 (d, J=8.6 Hz, 2H), 7.26 (s, 1H), 6.92 (d, J=8.6 Hz, 2H), 6.21 (dd, J=10.0, 4.9 Hz, 1H), 5.32-5.20 (m, 3H), 4.69 (d, J=4.8 Hz, 1H), 4.15-4.09 (m, 1H), 3.83 (s, 3H), 3.46 (q, J=7.3 Hz, 1H), 1.79 (d, J=7.3 Hz, 3H), 1.58 (d, J=4.3 Hz, 6H), 1.53 (s, 9H), 1.42 (s, 9H).

(3) Compound II-3→Compound III-2

To a cooled (−40° C.) solution of compound II-3 (395 mg, 0.487 mmol) in DMF (4 ml) was added phosphorous trichloride (0.047 ml, 0.536 mmol). After 15 min, phosphorous trichloride (0.047 ml, 0.536 mmol) was again added to the mixture. After the reaction mixture was stirred for 45 min at −40° C., the mixture was diluted with H$_2$O and EtOAc. The aqueous layer was extracted with ethyl acetate and the combined extracts were washed with water and brine, dried (MgSO$_4$), filtered, and concentrated in vacuo.

The residue was purified by silica gel chromatography to afford 326 mg of compound III-2 (84%).

$^1$H-NMR (CDCl$_3$) δ: 8.23 (br s, 1H), 8.13 (d, J=9.0 Hz, 1H), 7.34 (d, J=8.5 Hz, 2H), 7.31 (s, 1H), 6.91 (d, J=8.7 Hz, 2H), 5.99 (dd, J=9.0, 5.0 Hz, 1H), 5.30-5.12 (m, 3H), 4.97 (d, J=12.2 Hz, 1H), 4.27 (d, J=12.2 Hz, 1H), 4.01 (q, J=7.1 Hz, 1H), 3.82 (s, 3H), 1.65-1.56 (m, 9H), 1.41 (s, 9H).

Example 7

Synthesis of Compound III-2

[Chemical Formula 56]

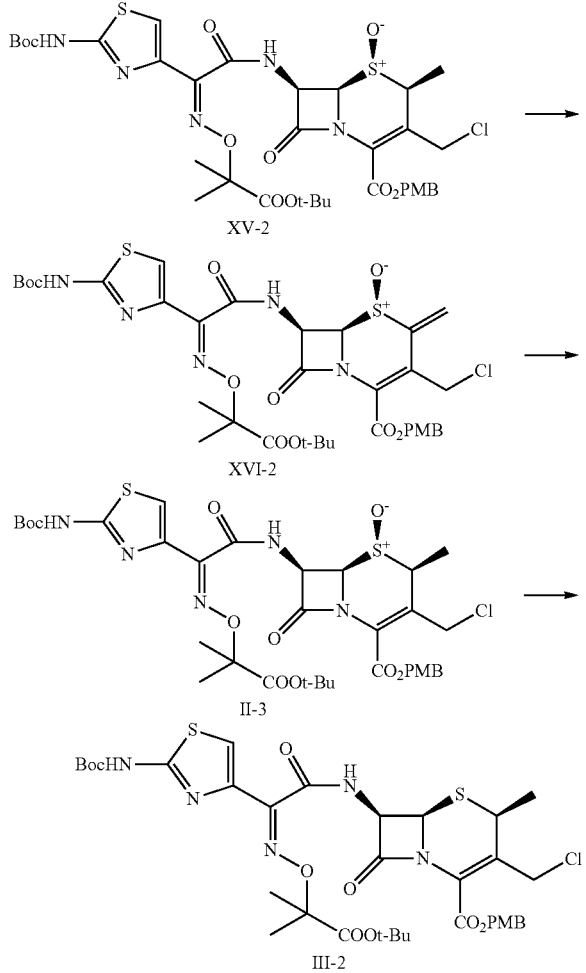

(1) Compound XV-2→Compound XVI-2 (as a Seed Crystal)

To a slurry of paraformaldehyde (0.57 g, 18.8 mmol) in N,N-dimethylacetamide (20 mL) was added diisopropylamine (2.68 mL, 18.8 mmol) and trifluoroacetic acid (2.90 mL, 37.7 mmol). After stirring at 60° C. for 0.5 hr, to the mixture was added the solution of Compound XV-2 (5.00 g, 6.28 mmol) in N,N-dimethylacetamide (17.5 mL). The mixture was stirred at 60° C. for 3 hr, poured into water and extracted with ethyl acetate. The organic layer was washed with water, dried (sodium sulfate) and concentrated in vacuo. The residue was purified by column chromatography on silica gel, eluted with ethyl acetate and n-hexane and concentrated. To the residue was added 2-propanol (25 mL) and the slurry was stirred at 50° C. for 0.5 hr to afford Compound XVI-2 (2.50 g, 49%) as a seed crystal.

(2) Compound XV-2→Compound XVI-2

A solution of paraformaldehyde (3.39 g, 113 mmol) and diisopropylamine (16.1 mL, 113 mmol) in N,N-dimethylacetamide (90 mL) was stirred at 60° C. for 10 min and then cooled in ice bath. To the solution were added trifluoroacetic acid (17.4 mL, 226 mmol) and compound XV-2 (30.0 g, 37.7 mmol). The mixture was stirred at 60° C. for 3 hr and then the precipitate was filtered and washed with acetonitrile (30 mL). To the resulting solution of mixture were added acetonitrile (120 mL), water (90 mL) and the seed crystal obtained above (1) of compound XVI-2 (30 mg) at room temperature and then stirred at the same temperature for 1.0 hr. To the mixture were added acetonitrile (150 mL) and water (150 mL) dropwise over 30 min. The mixture was stirred for 10 min at room temperature and then stirred in ice bath for 1.5 hr. The precipitated material was collected by filtration and washed with water (36 mL) and acetonitrile (54 mL). The solid was dried under air for 64 hr to afford compound XVI-2 as a crystal (19.99 g, 65.6%).

mp: 169-171° C.

$^1$H-NMR (DMSO-D$_6$) δ: 11.78 (1H, s), 8.57 (1H, d, J=8.0 Hz), 7.40 (1H, d, J=8.0 Hz), 7.40 (1H, d, J=8.0 Hz), 7.36 (1H, s), 6.95 (1H, d, J=8.0 Hz), 6.95 (1H, d, J=8.0 Hz), 6.54 (1H, s), 6.30 (1H, s), 6.12 (1H, dd, J=8.0, 4.0 Hz), 5.33-5.26 (2H, m), 5.21 (1H, d, J=4.0 Hz), 4.90 (1H, d, J=12.0 Hz), 4.66 (1H, d, J=12.0 Hz), 3.77 (3H, s), 1.50-1.38 (24H, m). diffraction angle (2-theta angles): 5.3°, 7.0°, 10.2°, 10.5°, 11.5°, 14.0°, 14.7°, 14.8°, 15.8°, 16.5°, 16.6°, 16.7°, 17.4°, 18.3°, 18.8°, 19.3°, 19.7°, 20.5°, 20.7°, 21.1°, 21.3°, 21.6°, 23.0°, 23.2°, 23.5°, 23.8°, 24.2°, 24.6°, 25.5°, 26.6°, 26.9°, 27.2°, 27.5°, 27.9°, 28.4°, 29.6°, 29.9°, 30.9°, 31.3°, 31.5°, 33.8°, 34.4°, 35.0°.

(3) Compound XVI-2→Compound II-3

To a solution of compound XVI-2 (5.00 g, 6.19 mmol) in methanol (50 mL), ethyl acetate (10 mL) and acetic acid (3.71 g, 61.9 mmol) with stirring at −12° C. was added sodium borohydride (0.24 g, 6.34 mmol) in N,N-dimethylacetamide (5 mL) over 30 min. The mixture was stirred at −15° C. for 0.5 hr. 10% aqueous solution of sodium chloride (75 mL), 75% sulfuric acid (1.50 g) and ethyl acetate (50 mL) were added to the mixture, and then an organic layer was separated. The organic layer was washed with 10% aqueous solution of sodium chloride (50 mL), and then an organic layer was separated. The organic layer was dried over sodium sulfate and filtered. The filtrate was concentrated to give crude compound II-3. The crude compound II-3 was purified by column chromatography on silica gel, eluted with ethyl acetate and n-hexane and concentrated to afford a purified amorphous compound II-3 (4.41 g, 88.0%).

$^1$H-NMR (DMSO-D$_6$) δ: 11.78 (1H, s), 8.49 (1H, d, J=8.0 Hz), 7.38 (1H, d, J=8.0 Hz), 7.38 (1H, d, J=8.0 Hz), 7.33 (1H, s), 6.95 (1H, d, J=8.0 Hz), 6.95 (1H, d, J=8.0 Hz), 6.08 (1H, dd, J=8.0, 4.0 Hz), 5.31-5.22 (2H, m), 5.23 (1H, d, J=4.0 Hz), 4.85 (1H, d, J=12.0 Hz), 4.44 (1H, d, J=12.0 Hz), 3.90 (1H, m), 3.76 (3H, s), 1.62 (1H, d, J=4.0 Hz), 1.48-1.38 (24H, m).

(4) Crystallization of Compound II-3

A solution of the amorphous compound II-3 (1.31 g, 1.62 mmol), in toluene (6 mL) and n-heptane (3 mL) was kept at 25° C. for 63 hr. The resulting precipitated material was collected by filtration. The solid was dried under air for 3 hr to afford compound II-3 (1.07 g, 81.7%) as a crystal.

mp: 122-123° C.

$^1$H-NMR (DMSO-D$_6$) δ: 11.78 (1H, s), 8.49 (1H, d, J=8.0 Hz), 7.38 (1H, d, J=8.0 Hz), 7.38 (1H, d, J=8.0 Hz), 7.33 (1H, s), 6.95 (1H, d, J=8.0 Hz), 6.95 (1H, d, J=8.0 Hz), 6.08 (1H, dd, J=8.0, 4.0 Hz), 5.31-5.22 (2H, m), 5.23 (1H, d, J=4.0 Hz), 4.85 (1H, d, J=12.0 Hz), 4.44 (1H, d, J=12.0 Hz), 3.90 (1H, m), 3.76 (3H, s), 1.62 (1H, d, J=4.0 Hz), 1.48-1.38 (24H, m).

X-ray diffraction angle (2-theta angles): 5.2°, 5.7°, 7.3°, 7.8°, 8.2°, 9.3°, 11.3°, 11.6°, 12.0°, 12.8°, 13.2°, 14.1°, 14.5°, 15.3°, 15.7°, 16.4°, 17.0°, 17.5°, 18.5°, 18.7°, 19.3°, 20.4°, 20.8°, 21.2°, 21.6°, 21.8°, 22.4°, 23.4°, 24.0°, 24.8°, 25.6°, 26.3°, 26.8°, 28.0°, 28.4°, 29.1°, 32.2°, 33.0°, 34.4°, 34.6°.

(5) Compound II-3→Compound III-2

To a solution of compound II-3 (3.0 g, 3.70 mmol) in N,N-dimethylacetamide (10.5 mL) was added phosphorus tribromide (1.10 g, 4.07 mmol) at 0° C. and then stirred at the same temperature for 0.5 hr. 10% aqueous solution of sodium chloride (30 mL) and ethyl acetate (33 mL) were added to the mixture, and then an organic layer was separated. The organic layer was washed with 10% aqueous solution of sodium chloride (30 mL), and then an organic layer was separated. The organic layer was concentrated to give crude compound III-2. The crude compound III-2 was purified by column chromatography on silica gel, eluted with ethyl acetate and n-hexane and concentrated to afford a purified amorphous compound III-2 (2.76 g, 94%).

$^1$H-NMR (DMSO-D$_6$) δ: 11.82 (1H, s), 9.53 (1H, d, J=8.0 Hz), 7.36 (1H, d, J=8.0 Hz), 7.36 (1H, d, J=8.0 Hz), 7.26 (1H, s), 6.94 (1H, d, J=8.0 Hz), 6.94 (1H, d, J=8.0 Hz), 5.88 (1H, dd, J=8.0, 4.0 Hz), 5.41 (1H, d, J=4.0 Hz), 5.28-5.17 (2H, m), 4.67 (1H, d, J=12.0 Hz), 4.49 (1H, d, J=12.0 Hz), 4.08 (1H, q, J=8.0 Hz), 4.02 (3H, s), 1.52 (1H, d, J=8.0 Hz), 1.46-1.38 (24H, m).

(6) Crystallization of Compound III-2 (as a Seed Crystal)

The amorphous compound III-2 was dissolved with ethyl acetate (3V) at room temperature. The solution was added n-heptane (6V) and was kept at 5° C. for about 1 hour. The resulting precipitated material was collected by filtration to afford Compound III-2 as a seed crystal.

(7) Crystallization of Compound III-2

To a solution of the amorphous compound III-2 (2.0 g) in n-heptane (12.9 mL) and ethyl acetate (6.0 mL) with stirring at 25° C. was added the seed crystal obtained above (5) of compound III-2 (10 mg). The mixture was stirred for 5.5 hr at room temperature. The precipitated material was collected by filtration and washed with heptane (4 mL) and ethyl acetate (1 mL). The solid was dried under air for 1 hr to afford compound III-2 (1.66 g, 83%) as a crystal.

mp: 122-124° C.

$^1$H-NMR (DMSO-D$_6$) δ: 11.82 (1H, s), 9.53 (1H, d, J=8.0 Hz), 7.36 (1H, d, J=8.0 Hz), 7.36 (1H, d, J=8.0 Hz), 7.26 (1H, s), 6.94 (1H, d, J=8.0 Hz), 6.94 (1H, d, J=8.0 Hz), 5.88 (1H, dd, J=8.0, 4.0 Hz), 5.41 (1H, d, J=4.0 Hz), 5.28-5.17 (2H, m), 4.67 (1H, d, J=12.0 Hz), 4.49 (1H, d, J=12.0 Hz), 4.08 (1H, q, J=8.0 Hz), 4.02 (3H, s), 1.52 (1H, d, J=8.0 Hz), 1.46-1.38 (24H, m).

X-ray diffraction angle (2-theta angles): 4.8°, 6.2°, 7.7°, 8.1°, 8.8°, 9.1°, 9.6°, 10.0°, 10.6°, 11.4°, 12.3°, 14.4°, 14.9°, 15.7°, 16.4°, 16.9°, 17.3°, 17.8°, 18.4°, 19.3°, 19.6°, 20.2°, 21.4°, 21.8°, 22.1°, 24.4°, 25.0°, 25.3°, 25.9°, 28.8°, 34.4°.

Example 8

Synthesis of Compound VII-2

[Chemical Formula 57]

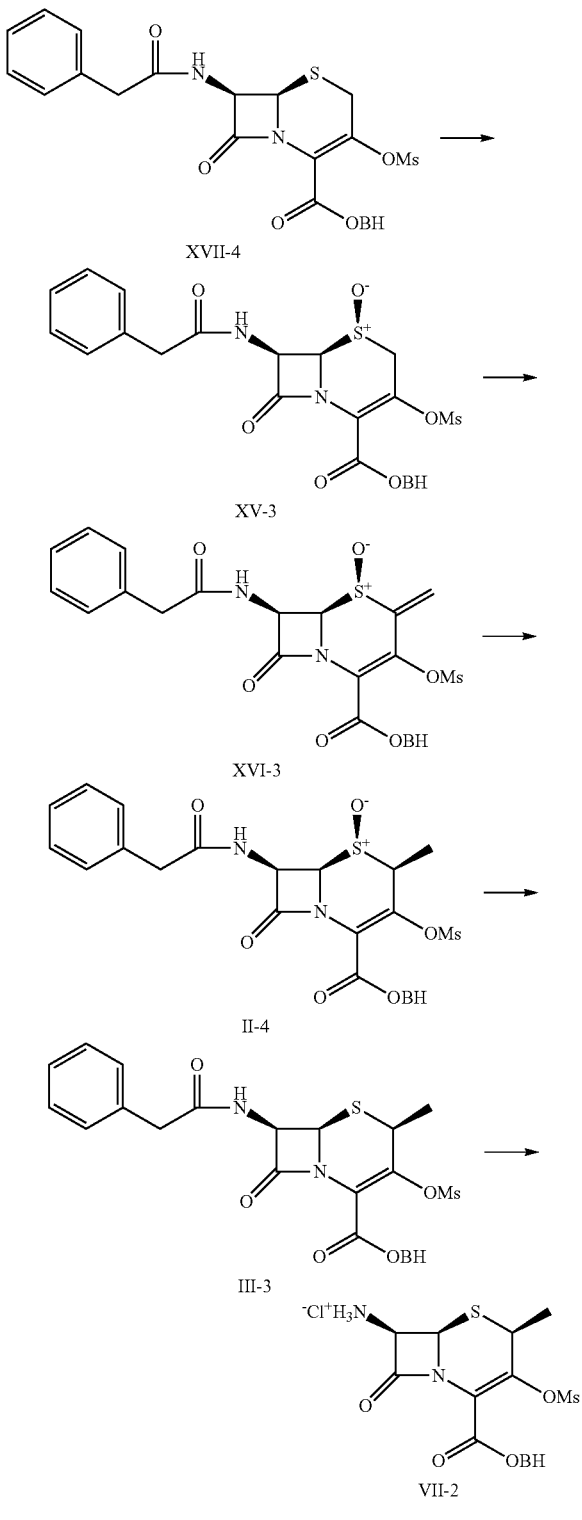

(1) Compound XVII-4→Compound XV-3

To a cooled (0° C.) solution of compound XVII-4 (17.4 g, 30.0 mmol) in DMA (200 ml) was added 39% peracetic acid (5.69 ml, 33.0 mmol).

After stirring for 1 hr at 0° C., the mixture was quenched by 50 mL of 10% sodium bisulfite aqueous solution. The resulting solid was collected by filtration and washed with water and isopropanol to afford 17.4 g of compound XV-3 (98%).

$^1$H-NMR (DMSO-D$_6$) δ: 8.57 (d, J=8.1 Hz, 1H), 7.50 (d, J=7.7 Hz, 2H), 7.42-7.21 (m, 13H), 6.97 (s, 1H), 5.91 (dd, J=8.1, 4.5 Hz, 1H), 5.03 (d, J=4.5 Hz, 1H), 4.20 (d, J=18.1 Hz, 1H), 4.01 (d, J=18.1 Hz, 1H), 3.69 (d, J=14.0 Hz, 1H), 3.55 (d, J=14.0 Hz, 1H), 3.12 (s, 3H).

(2) Compound XV-3→Compound XVI-3

To a solution of compound XV-3 (17 g, 28.6 mmol) in DMF (170 ml) was added dimethylamine hydrochloride (2.33 g, 28.6 mmol) and 36% to 38% formalin (4.26 ml, 57.2 mmol). After stirring for 30 min at 50° C., the resulting mixture was poured into water then the resulting solid was collected by filtration to afford 13.2 g of compound XVI-3 (76%)

$^1$H-NMR (DMSO-D$_6$) δ: 8.59 (d, J=8.3 Hz, 1H), 7.53 (d, J=7.7 Hz, 2H), 7.42-7.23 (m, 14H), 6.95 (s, 1H), 6.51 (s, 1H), 6.45 (s, 1H), 6.05 (dd, J=8.3, 5.0 Hz, 1H), 5.25 (d, J=5.0 Hz, 1H), 3.69 (d, J=14.1 Hz, 1H), 3.58 (d, J=14.1 Hz, 1H), 3.23 (s, 3H).

(3) Compound XVI-3→Compound II-4

Compound XVI-3 (12.5 g, 20.6 mmol) was used to synthesize compound II-4 in the same way as in (4) of Example 3.

Yielded amount: 9.4 g (75%)

$^1$H-NMR (DMSO-D$_6$) δ: 8.61 (d, J=8.1 Hz, 1H), 7.49 (d, J=7.7 Hz, 2H), 7.44-7.22 (m, 13H), 6.95 (s, 1H), 5.94 (dd, J=3.5, 8.1 Hz, 1H), 5.18 (d, J=3.5 Hz, 1H), 4.06 (q, J=7.7 Hz, 1H), 3.68 (d, J=14.3 Hz, 1H), 3.57 (d, J=14.3 Hz, 1H), 3.04 (s, 3H), 1.55 (d, J=7.7 Hz, 3H).

(4) Compound II-4→Compound III-3

Compound II-4 (9.39 g, 15.4 mmol) was used to synthesize compound III-3 in the same way as in (3) of Example 6.

Yielded amount: 9.4 g (quantitative)

$^1$H-NMR (DMSO-D$_6$) δ: 9.22 (d, J=8.4 Hz, 1H), 7.48 (d, J=7.8 Hz, 2H), 7.42-7.19 (m, 13H), 6.90 (s, 1H), 5.83 (dd, J=8.4, 5.0 Hz, 1H), 5.41 (d, J=5.0 Hz, 1H), 4.26 (q, J=7.1 Hz, 1H), 3.60-3.50 (m, 2H), 3.07 (s, 3H), 1.48 (d, J=7.1 Hz, 3H).

(5) Compound III-3 Compound VII-2

To a cooled (−20° C.) slurry of phosphorus pentachloride (4.01 g, 19.2 mmol) in dichloromethane (60.0 ml) was added pyridine (1.67 ml, 21.2 mmol) followed by compound III-3 (5.7 g, 9.62 mmol). After the mixture was stirred for 45 min at 0° C., the mixture was cooled to −40° C. then MeOH (23.4 ml, 577 mmol) was added to this mixture in one portion. The mixture was warmed to room temperature and diluted with water and dichloromethane. The aqueous layer was extracted with dichloromethane. The combined organic layers were washed with water and brine, dried over MgSO$_4$, filtered. To this mixture was added 4 mmol/1 HCl in EtOAc (3.61 ml) then this solution was concentrated in vacuo to afford compound VII-2.

Example 9

Synthesis of Compound VII-4

[Chemical Formula 58]

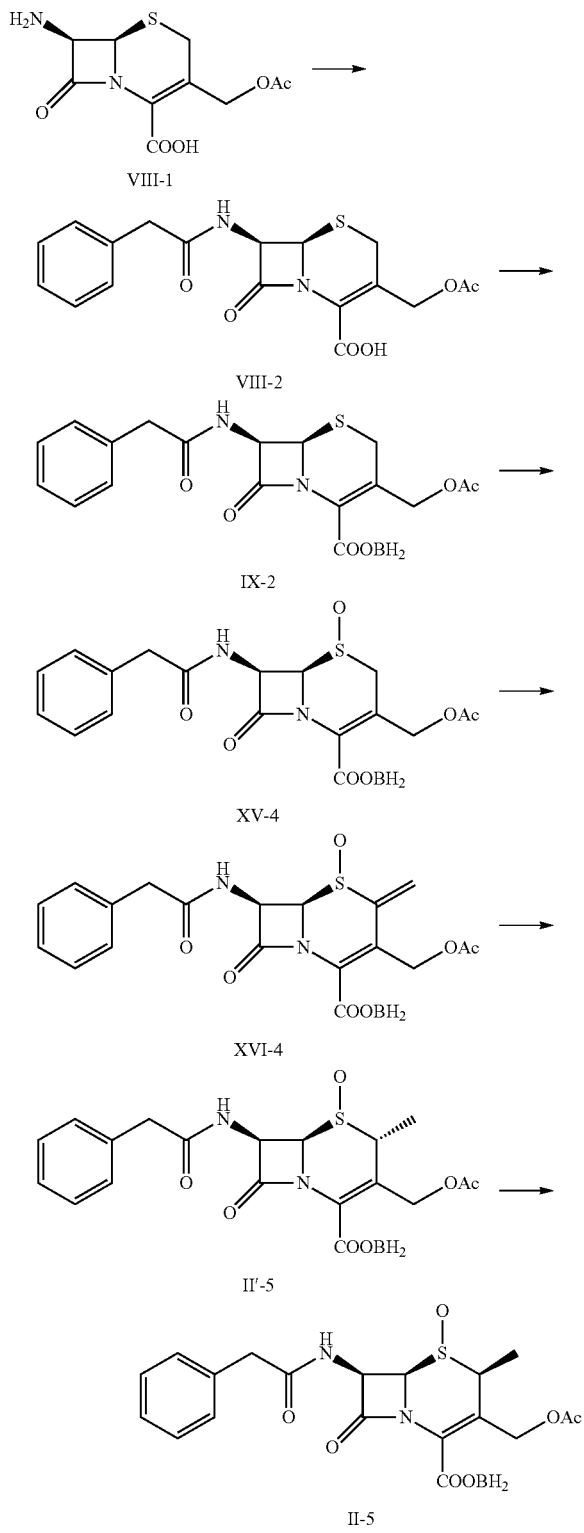

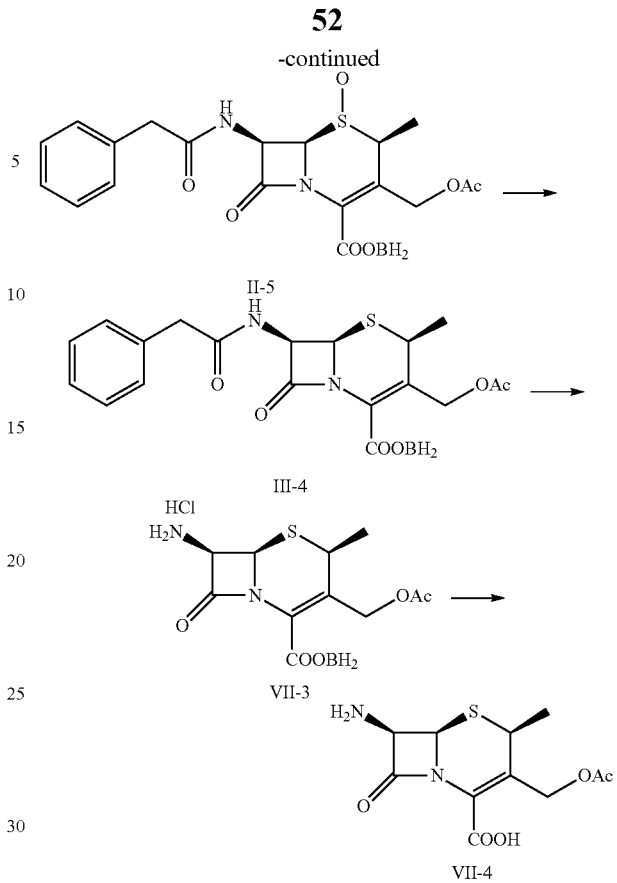

(1) Compound VIII-1→Compound VIII-2

To a solution of compound VIII-1 (54.5 g, 200 mmol) in MeOH (100 ml) was added dropwise triethylamine (69.3 ml, 500 mmol) for 15 minutes at −30° C. To the reaction mixture, 2-phenylacetyl chloride (31.7 ml, 240 mmol) was added dropwise for 20 minutes at −30° C. The reaction mixture was stirred at −20° C. for 15 minutes, poured into 2N—HCl and extracted with EtOAc. The EtOAc layer was washed successively with $H_2O$ and brine and then dried. Evaporation under reduced pressure gave compound VIII-2 (56.3 g, 72%).

$^1$H-NMR ($d_6$-DMSO) δ: 2.03 (3H, s), 3.49, 3.57 (2H, ABq, J=14.6 Hz), 3.49, 3.61 (2H, ABq, J=18.4 Hz), 4.69, 5.00 (2H, ABq, J=12.8 Hz), 5.08 (1H, d, J=5.2 Hz), 5.68 (1H, dd, J=8.4, 4.8 Hz), 7.21-7.32 (15H, m), 9.09 (1H, d, J=8.4 Hz).

(2) Compound VIII-2→Compound IX-2

To a solution of compound VIII-2 (19.5 g, 50 mmol) in THF (150 ml) was added a solution of diphenyldiazomethane (69.3 ml, 500 mmol) in THF (50 ml). The reaction mixture was stirred for 2 hours at room temperature, evaporated under reduced pressure. The residue was added THF and i-$Pr_2O$. The resulting solid was collected by filtration to give compound IX-2 (27.6 g, 99%). $^1$H-NMR (CDCl3) δ: 1.99 (3H, s), 3.31, 3.49 (2H, ABq, J=18.4 Hz), 3.61, 3.65 (2H, ABq, J=16.2 Hz), 4.76, 5.00 (2H, ABq, J=13.6 Hz), 4.94 (1H, d, J=4.8 Hz), 5.85 (1H, dd, J=5.2, 9.2 Hz), 6.16 (1H, d, J=9.2 Hz), 6.92 (1H, s), 7.25-7.41 (15H, m).

(3) Compound IX-2→Compound XV-4

To a solution of compound IX-2 (27.5 g, 49.5 mmol) in $CH_2Cl_2$ (200 ml) was added dropwise a solution of m-Chloroperbenzoic acid (13.1 g, 49.5 mmol, 65% wt) in $CH_2Cl_2$ (50 ml) for 20 minutes at −78° C. The reaction mixture was stirred for 20 minutes at −78° C. To the reaction mixture was added a solution of Na$_2$S$_2$O$_3$ (2.35 g, 14.8 mmol) in H$_2$O (100 ml) and i-Pr$_2$O and a solution of NaHCO$_3$ (6.23 g, 74.2 mmol) in H$_2$O (100 ml). The mixture was concentrated under reduced pressure to give a solid. The solid was collected by filtration to give compound XV-4 (27.7 g, 98%). $^1$H-NMR (CDCl3) δ: 2.01 (3H, s), 3.18, 3.79 (2H, ABq, J=18.8 Hz), 3.62, 3.66 (2H, ABq, J=15.8 Hz), 4.44 (1H, d, J=4.4 Hz), 4.71, 5.27 (2H, ABq, J=14.0 Hz), 6.10 (1H, dd, J=4.8, 10.0 Hz), 6.70 (1H, d, J=10.0 Hz), 6.94 (1H, s), 7.26-7.46 (15H, m).

(4) Compound XV-4→Compound XVI-4

To a solution of compound XV-4 (27.68 g, 48.3 mmol) and dimethylamine hydrochloride (3.94 g, 48.3 mmol) in DMF (150 ml) was added 37%-formaline (7.2 ml, 97 mmol) at room temperature. The reaction mixture was stirred for 4 hours at 70° C. The reaction mixture was poured into H$_2$O, THF and i-Pr$_2$O (THF:i-Pr$_2$O=1:2) to give a solid. The solid was collected by filtration. The solid was dissolved in THF. The THF solution was added MgSO$_4$ and activated carbon. The insoluble material was filtered off. The filtrate was evaporated to give compound XVI-4 (23.01 g, 81%)

$^1$H-NMR (d$_6$-DMSO) δ: 1.90 (3H, s), 3.58, 3.68 (2H, ABq, J=14.0 Hz), 4.70, 5.18 (2H, ABq, J=12.6 Hz), 5.09 (1H, d, J=4.8 Hz), 5.98 (1H, dd, J=5.2, 8.4 Hz), 6.22 (1H, s), 6.39 (1H, s), 6.98 (1H, s), 7.30-7.49 (15H, m), 8.53 (1H, d, J=8.4 Hz).

(5) Compound XVI-4→Compound II'-5 and Compound II-5

To a solution of NaBH$_4$ (1.03 g, 27.2 mmol) in MeOH (330 ml) was added dropwise a solution of compound XVI-4 (13.3 g, 22.7 mmol) in THF (330 ml) (Compound 5 was dissolved in THF at 60° C. and then cooled to room temperature.) for 20 minutes at −40° C. The reaction mixture was stirred for 20 minutes at −35° C. The reaction mixture was added TFA (4.19 ml, 54.4 mmol) and concentrated under reduced pressure to give a solid. The solid was collected by filtration to give compound II-5 (9.92 g, 75%). Compound II-5:Compound II'-5=27.8:1 (HPLC Analysis)

$^1$H-NMR (d$_6$-DMSO) δ: 1.55 (3H, d, J=7.6 Hz), 1.95 (3H, s), 3.58, 3.68 (2H, ABq, J=14.0 Hz), 3.76 (1H, q, J=7.2 Hz), 4.49, 5.13 (2H, ABq, J=13.2 Hz), 5.08 (1H, d, J=4.8 Hz), 5.93 (1H, dd, J=4.8, 8.4 Hz), 6.94 (1H, s), 7.21-7.50 (15H, m), 8.47 (1H, d, J=8.4 Hz).

Compound II-5 was also obtained from compound XVI-4 under the condition below.

TABLE 2

| Reagent | Solvent | time | ratio (II-5:II'-5) | conversion of II-5 (%) |
|---|---|---|---|---|
| H2 gas/ Rh (0.25 eq.) | THF (20 V)/ AcOH (10 V) | 30 min. | 6.4:1 | 34 |

The ratio and the conversion were determined by NMR.

(6) Compound II-5→Compound III-4

To a solution of compound II-5 (10.6 g, 18.1 mmol) in DMF (80 ml) was added PBr$_3$ (3.41 ml, 36.2 mmol) at −40° C. The reaction mixture was stirred at −40° C. for 20 minutes, poured into H$_2$O and extracted with EtOAc. The EtOAc layer was washed successively with H$_2$O and Brine and then dried. The EtOAc solution was evaporated under reduced pressure. The residue was added i-Pr$_2$O. The resulting solid was collected by filtration to give compound III-4 (9.08 g, 880%).

$^1$H-NMR (CDCl3) δ: 1.37 (3H, d, J=7.2 Hz), 1.98 (3H, s), 3.64, 3.68 (2H, ABq, J=16.4 Hz), 3.79 (1H, q, J=7.2 Hz), 4.73, 5.15 (2H, ABq, J=13.6 Hz), 5.08 (1H, d, J=4.8 Hz), 5.78 (1H, dd, J=4.8, 9.2 Hz), 6.07 (1H, d, J=9.2 Hz), 6.92 (1H, s), 7.26-7.39 (15H, m).

(7) Compound III-4→Compound VII-3

To a suspension of phosphorus pentachloride (4.92 g, 23.6 mmol) in CH$_2$Cl$_2$ (90 ml) was added pyridine (2.17 ml, 26.8 mmol) at 0° C. The reaction mixture was added compound III-4 (8.99 g, 25.8 mmol) at 0° C. and the mixture was stirred for 1 hour at 0° C. The reaction mixture was added MeOH (40 ml) in one portion at −50° C., and the mixture was stirred for 20 minutes at 0° C. The reaction mixture was added H$_2$O and CH$_2$Cl$_2$ layer was separated. The CH$_2$Cl$_2$ layer was washed successively with H$_2$O and aqueous NaHCO$_3$ solution and then dried. The solution was added 4M/L-HCl/EtOAc (5.9 ml, 23.6 mmol) and concentrated under reduced pressure to give a solid. The solid was collected by filtration to give compound VII-3 (6.62 g, 85%).

$^1$H-NMR (d$_5$-DMSO) δ: 1.48 (3H, d, J=7.2 Hz), 1.95 (3H, s), 4.16 (1H, q, J=6.8 Hz), 4.61, 4.98 (2H, ABq, J=13.2 Hz), 5.26 (1H, d, J=4.8 Hz), 5.93 (1H, d, J=4.8 Hz), 6.94 (1H, s), 7.28-7.46 (15H, m), 9.05 (2H, brs).

(8) Compound VII-3→Compound VII-4

To a solution of compound VII-3 (6.43 g, 13.2 mmol) and anisole (4.31 ml, 39.4 mmol) in CH$_2$Cl$_2$ (30 ml) was added TFA (30 ml) at 0° C. The reaction mixture was stirred at 0° C. for 50 minutes. The mixture was added the EtOAc and H$_2$O. The pH of solution was adjusted from −0.3 to 4 by 20%-aqueous Na$_2$CO$_3$ solution to give a solid. The solid was collected by filtration to give compound VII-4 (3.85 g, 102%).

$^1$H-NMR (d$_6$-DMSO) δ: 1.45 (3H, d, J=7.2 Hz), 2.01 (3H, s), 3.95 (1H, q, J=7.2 Hz), 4.76 (1H, d, J=4.8 Hz), 4.60, 5.13 (2H, ABq, J=11.0 Hz), 5.11 (1H, d, J=4.8 Hz).

Example 10

Synthesis of Compound VII-6

[Chemical Formula 59]

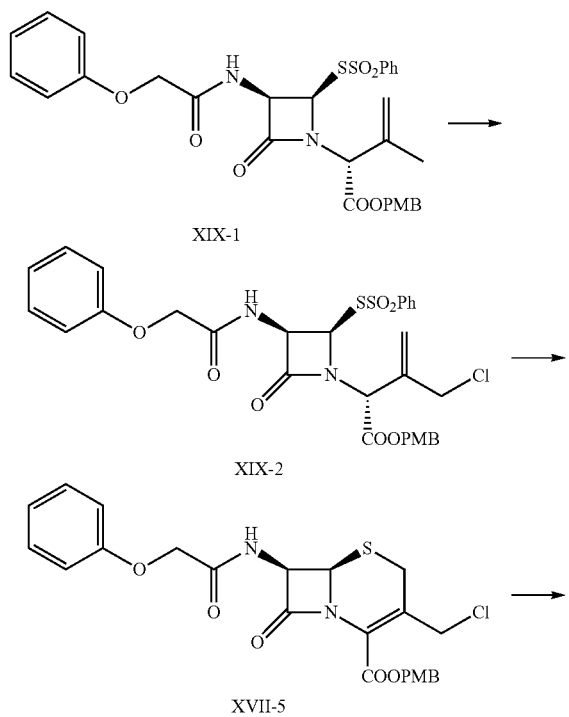

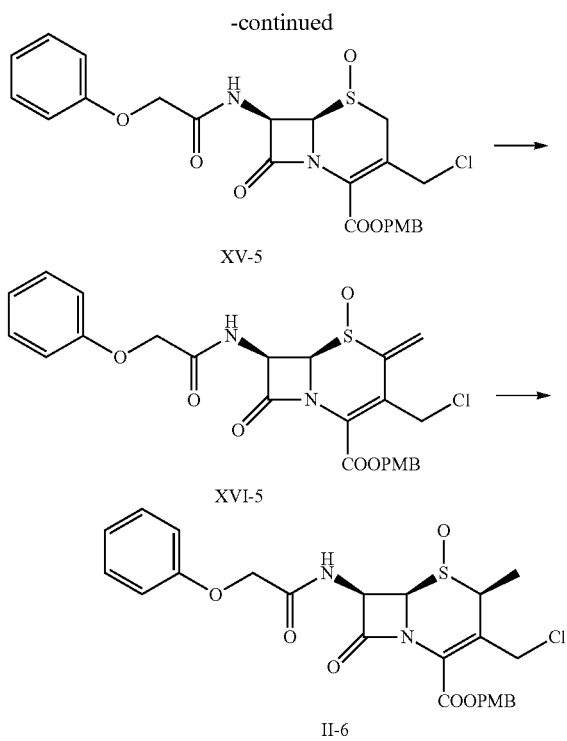

XV-5

XVI-5

II-6

(1) Compound XIX-1→Compound XIX-2→Compound XVII-5

To a solution of compound XIX-1 (EP114729) (1.43 g, 2.34 mmol) and calcium oxide (394 mg, 7.0 mmol) in THF (30 ml) was added dropwise 1M/L-Cl$_2$/CCl$_4$ (3.93 ml, 3.93 mmol) in several times at room temperature. The reaction mixture was stirred at room temperature for 50 minutes. The insoluble materials were filtered off. The filtrate was evaporated under reduced pressure to give crude compound XIX-2 (1.68 g).

To the solution of crude compound XIX-2 (1.49 g) in DMF (15 ml) was added 1M/L-NH3/MeOH (4.15 ml, 4.15 mmol) at −50° C. The reaction mixture was stirred at −50° C. for 2.5 hours, poured into diluted Hydochloric acid and extracted with EtOAc. The EtOAc layer was washed successively with H$_2$O and brine and then dried. The EtOAc solution was evaporated under reduced pressure. The residue was added EtOAc and i-Pr$_2$O. The resulting solid was collected by filtration to give compound XVII-5 (637 mg, 61%). $^1$H-NMR (CDCl3) δ: 3.48, 3.65 (2H, ABq, J=18.8 Hz), 3.81 (3H, s), 4.43, 4.53 (2H, ABq, J=11.6 Hz), 4.57 (2H, s), 5.01 (1H, d, J 4.8 Hz), 5.25 (2H, s), 5.92 (1H, dd, J=9.2, 5.2 Hz), 6.89-7.37 (10H, m).

(2) Compound XVII-5→Compound XV-5

Compound XVII-5 (12.55 g, 25 mmol) was used to synthesize compound XV-5 (11.2 g, 86%) in the same way as in (3) of Example 9.

$^1$H-NMR (d$_6$-DMSO) δ: 3.76 (3H, s), 3.76, 4.01 (2H, ABq, J=18.2 Hz), 4.54, 4.65 (2H, ABq, J=11.6 Hz), 4.69 (2H, s), 5.02 (1H, d, J=4.4 Hz), 5.22, 5.29 (2H, ABq, J=11.8 Hz), 6.07 (1H, dd, J=4.4, 9.6 Hz), 6.94-7.01 (5H, m), 7.29-7.39 (4H, m), 8.18 (1H, d, J=9.6 Hz).

(3) Compound XV-5→Compound XVI-5 To a solution of compound XV-5 (5.19 g, 10 mmol) in dioxane (50 ml) was added paraformaldehyde (3.0 g, 100 mmol) and TFA (2.31 ml, 30 mmol) and diisopropylamine (2.85 ml, 20 mmol) at room temperature. The reaction mixture was stirred at 65° C. for 3.5 hours. The reaction mixture was added activated carbon and then filtered. The filtrate was added MeOH to give a solid. The solid was collected by filtration. The solid was added H$_2$O and extracted with mixture of EtOAc and THE'. The combined Organic layer was washed successively with H$_2$O and Brine and then dried. Evaporation under reduced pressure gave Compound XVI-5 (3.11 g, 59%).

$^1$H-NMR (d$_6$-DMSO) δ: 3.76 (3H, s), 4.70 (2H, s), 4.66, 4.90 (2H, ABq, J=12.0 Hz), 5.16 (1H, d, J=5.2 Hz), 5.27, 5.32 (2H, ABq, J=13.0 Hz), 6.12 (1H, dd, J=4.8, 9.6 Hz), 6.33 (1H, s), 6.57 (1H, s), 6.94-7.01 (5H, m), 7.30-7.41 (4H, m), 8.24 (1H, d, J=9.6 Hz).

(4) Compound XVI-5→Compound II-6

To a solution of NaBH$_4$ (45 mg, 1.2 mmol) in MeOH (10 ml) was added dropwise a solution of compound XVI-5 (531 mg, 1 mmol) in THE (330 ml) (Compound XVI-5 was dissolved in THF at 60° C. and then cooled to room temperature.) for 15 minutes at −40° C. The reaction mixture was stirred for 30 minutes at −40° C., poured into 2N—HCl and extracted with EtOAc. The EtOAc layer was washed successively with H$_2$O and Brine and then dried. Evaporation under reduced pressure gave Compound II-6 (512 g, 960).

2β:2α=25:1 (NMR)

$^1$H-NMR (d$_6$-DMSO) δ: 1.63 (3H, d, J=7.6 Hz), 3.76 (3H, s), 3.90 (1H, q, J=7.6 Hz), 4.44, 4.82 (2H, ABq, J=12.4 Hz), 4.68 (2H, s), 5.17 (1H, d, J=4.8 Hz), 5.22, 5.30 (2H, ABq, J=12.0 Hz), 6.08 (1H, dd, J=4.8, 9.6 Hz), 6.94-7.01 (5H, m), 7.29-7.38 (4H, m), 8.24 (1H, d, J=9.6 Hz).

Example 11

Synthesis of Compound III-5

[Chemical Formula 60]

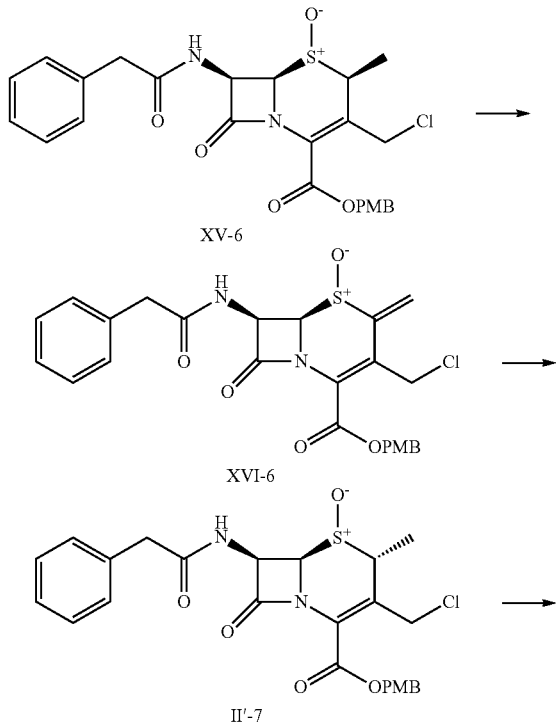

XV-6

XVI-6

II'-7

-continued

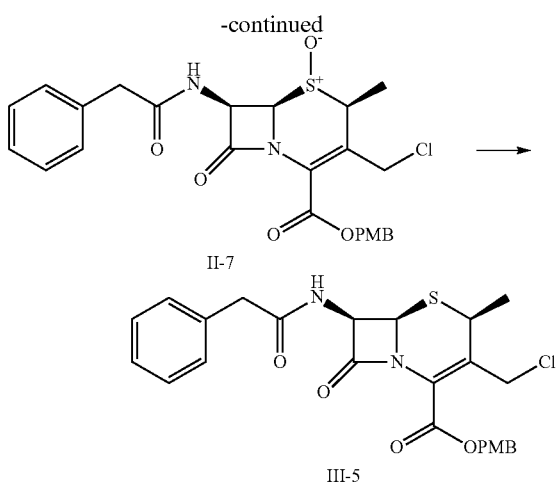

(1) Compound XV-6→Compound XVI-6

To a suspension of compound XV-6 (940 g, 1.85 mol) in N,N-dimethylacetamide (14.1 L) was added paraformaldehyde (278 g, 9.26 mol, 5 eq), trifluoroacetic acid (428 mL, 5.56 mol, 3 eq) and diisopropylamine (264 mL, 1.85 mol, 1 eq). The resulting suspension was stirred at 65~68° C., and the mixture gradually became solution. After stirring for 6 hours, the reaction mixture was stirred at 20-25° C. To the reaction mixture was added methanol (2.82 L) dropwise for 10 minutes and stirred at room temperature for 30 minutes. To the mixture was added water (1.88 L) dropwise for 5 minutes, and the mixture was stirred at room temperature. After stirring for 1 hour, the mixture was left at room temperature overnight. The precipitation was collected by filtration and washed with water (1.88 L) and methanol (2.82 L) respectively. The obtained crystal was dried under air to afford compound XVI-6 (499 g, 51.9% yield). $^1$H-NMR (DMSO-$d_6$) δ: 8.50 (1H, d, J=8.4 Hz), 7.40-7.23 (7H, m), 6.95 (2H, d, J=8.5 Hz), 6.48 (1H, d, J=1.0 Hz), 6.28 (1H, d, J=1.0 Hz), 5.91 (1H, dd, J=8.3, 5.0 Hz), 5.29 (2H, ABq, J=12.0 Hz), 5.05 (1H, d, J=5.0 Hz), 4.87 (1H, d, J=11.9 Hz), 4.62 (1H, d, J=11.9 Hz), 3.76 (3H, s), 3.68 (1H, d, J=14.2 Hz), 3.58 (1H, d, J=14.2 Hz).

(2) Compound XVI-6→Compound II-7 and Compound II'-7

Compound XVI-6 (408 g, 0.786 mol) was dissolved to N-methylpyrrolidone (4.08 L) at 65° C. and the resulting solution was cooled at room temperature. To methanol (8.16 L) was added sodium borohydride (17.8 g, 0.472 mol, 0.6 eq) at −50° C. To a mixture of sodium borohydride and methanol, N-methylpyrrolidone solution containing compound XVI-6 was added dropwise for 70 minutes at −50 to −40° C. The resulting mixture was stirred at this temperature for 1 hour. To the reaction mixture was added trifluoroacetic acid (145 mL, 1.89 mol, 2.4 eq) followed by water (2.04 L) dropwise for 6 minutes. The mixture was stirred at room temperature for 2 hours. The precipitation was collected by filtration and washed with water (1.02 L) and ethanol (1.22 L) respectively. The obtained solid was dried under air to afford a mixture of compound II-7 and compound II'-7 (376 g, 92.4% yield). $^1$H-NMR indicated II-7: II'-7=13.7:1

$^1$H-NMR (DMSO-$d_6$) δ: 8.47 (1H, d, J=8.3 Hz), 7.36-7.20 (7H, m), 6.95-6.92 (2H, m), 5.84 (1H, dd, J=8.4, 4.9 Hz), 5.28 (1H, d, J=11.8 Hz), 5.20 (1H, d, J=11.8 Hz), 5.05 (1H, dd, J=4.8, 1.5 Hz), 4.78 (1H, d, J=12.3 Hz), 4.39 (1H, d, J=12.3 Hz), 3.81 (1H, q, J=7.6 Hz), 3.74 (3H, s), 3.66 (1H, d, J=14.1 Hz), 3.54 (1H, d, J=14.1 Hz), 1.60 (3H, d, J=7.5 Hz).

(3) Compound II-7→Compound III-5

To the suspension of a mixture of compound II-7 and compound II'-7 (900 g, 1.74 mol) in N,N-dimethylformamide (4.50 L) was added phosphorus trichloride (228 mL, 2.61 mol, 1.5 eq) dropwise for 35 minutes at −40° C. The reaction mixture became solution gradually. After stirring at −30 to −35° C. for 70 minutes, reaction mixture was poured into stirred mixture of dichloromethane (9.00 L) and ice-cold water (9.00 L). The organic layer was washed with water (9.00 L) and 10% aqueous solution of sodium chloride (5.40 L). The aqueous layers were extracted with dichloromethane (2.70 L) successively. The combined organic layers were dried over MgSO$_4$ and filtrated. The filtrate was concentrated to give 2.18 kg of brown solid. To the residue was added ethyl acetate (2.70 L) and resulting suspension was stirred at 35° C. for 30 minutes. To the suspension was added diisopropyl ether (2.70 L) and stirred at 35° C. for 30 minutes and room temperature for 75 minutes. The suspension was left at 5° C. overnight. The precipitation was collected by filtration and washed with ethyl acetate/diisopropyl ether (1/1, 3.60 L). The solid was dried under air to afford compound III-5 (605 g, 69.4%).

$^1$H-NMR (DMSO-$d_6$) δ: 9.16 (1H, d, J=8.4 Hz), 7.36-7.21 (7H, m), 6.95-6.91 (2H, m), 5.68 (1H, dd, J=8.3, 4.9 Hz), 5.29-5.24 (2H, m), 5.17 (1H, d, J=11.9 Hz), 4.63 (1H, d, J=12.2 Hz), 4.46 (1H, d, J=12.0 Hz), 4.05 (1H, q, J=7.2 Hz), 3.74 (3H, s), 3.58-3.51 (2H, m), 1.53 (3H, d, J=7.3 Hz).

The invention claimed is:

1. A process for preparing a compound of formula (XVI) or a salt thereof,

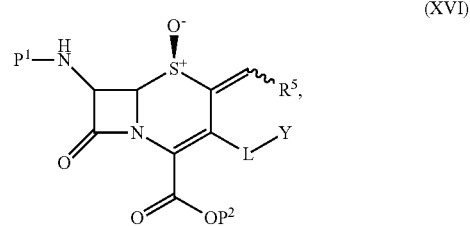

wherein, $R^5$ is hydrogen;

Y is halogen;

L is lower alkylene or lower alkenylene;

$P^1$ is acyl, phthalimide, optionally substituted aralkanoyl, optionally substituted aralkyl, optionally substituted arylimino, optionally substituted lower alkylimino, or tri-lower alkylsilyl;

$P^2$ is lower alkyl, alkylcarbonyloxymethyl in which the alkyl group is lower alkyl, optionally substituted aralkyl, or silyl groups; and the wavy line means that the bond is in cis or trans configuration, or a mixture thereof;

provided that -L-Y is not —CH$_2$—O—C(=O)—CH$_3$, which comprises:

reacting aldehyde, amino acid and a compound of formula (XV) or a salt thereof,

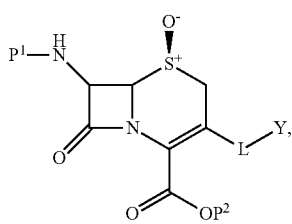 (XV)

wherein, each symbol is as defined above,
to give the compound of the formula (XVI) or a salt thereof.

2. A process for preparing a compound of formula (II) or a salt thereof,

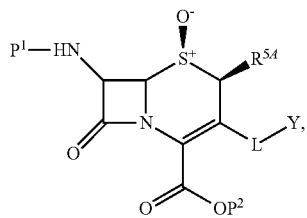 (II)

wherein,
$R^{5A}$ is lower alkyl;
Y is halogen;
L is lower alkylene or lower alkenylene;
$P^1$ is acyl, phthalimide, optionally substituted aralkanoyl, optionally substituted aralkyl, optionally substituted arylimino, optionally substituted lower alkylimino, or tri-lower alkylsilyl; and
$P^2$ is lower alkyl, alkylcarbonyloxymethyl in which the alkyl group is lower alkyl, optionally substituted aralkyl, or silyl groups,
which comprises:
reduction of a compound of formula (XVI)' or a salt thereof,

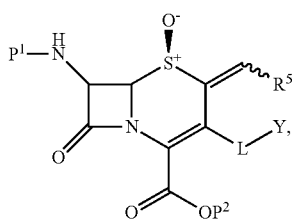 (XVI)' wherein,
$R^5$ is hydrogen or lower alkyl; and
the wavy line means that the bond is in cis or trans configuration, or a mixture thereof,
provided that -L-Y is not —CH$_2$—O—C(=O)—CH$_3$; and
the other symbols are as defined above,
to give the compound of the formula (II) or a salt thereof.

3. A process for preparing a compound of formula (III) or a salt thereof,

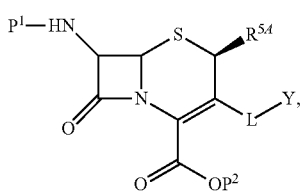 (III)' wherein,
$R^{5A}$ is lower alkyl;
Y is halogen;
L is lower alkylene or lower alkenylene;
$P^1$ is acyl, phthalimide, optionally substituted aralkanoyl, optionally substituted aralkyl, optionally substituted arylimino, optionally substituted lower alkylimino, or tri-lower alkylsilyl; and
$P^2$ is lower alkyl, alkylcarbonyloxymethyl in which the alkyl group is lower alkyl, optionally substituted aralkyl, or silyl groups,
which comprises:
reduction of a compound of formula (II) or a salt thereof,

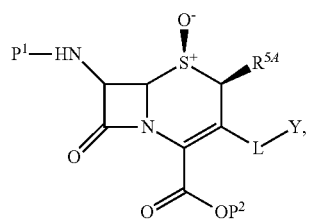 (II)

wherein each symbol is as defined above,
to give the compound of the formula (III) or a salt thereof.

4. The process for preparing a compound of the formula (III) or a salt thereof according to claim 3, wherein the compound of the formula (II) or a salt thereof is obtained by a process comprising:
reduction of a compound of formula (XVI)' or a salt thereof,

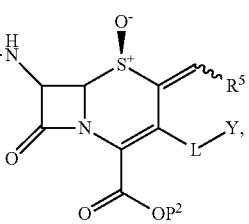 (XVI)' wherein,
$R^5$ is hydrogen or lower alkyl;
Y is halogen;
L is lower alkylene or lower alkenylene;
$P^1$ is acyl, phthalimide, optionally substituted aralkanoyl, optionally substituted aralkyl, optionally substituted arylimino, optionally substituted lower alkylimino, or tri-lower alkylsilyl;
$P^2$ is lower alkyl, alkylcarbonyloxymethyl in which the alkyl group is lower alkyl, optionally substituted aralkyl, or silyl groups; and the wavy line means that the bond is in cis or trans configuration, or a mixture thereof, provided that -L-Y is not —CH₂—O—C(=O)—CH₃,
to give the compound of the formula (II) or a salt thereof.

5. The process for preparing a compound of the formula (II) or a salt thereof according to claim 2, from the compound of the formula (XVI)':

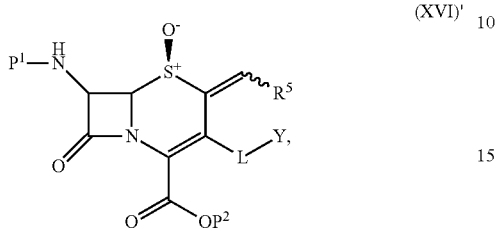

(XVI)' wherein each symbol is as defined above,
or a salt thereof obtained by a process, which comprises:
reacting aldehyde, amino acid and a compound of formula (XV) or a salt thereof,

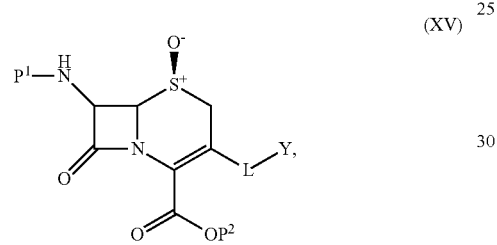

(XV)

wherein, each symbol is as defined above,
to give the compound of the formula (XVI)' or a salt thereof.

6. The process of claim 2, wherein $R^{5A}$ is methyl.
7. The process of claim 6, wherein L is —CH₂—.
8. The process of claim 7, wherein $P^1$ is acyl.
9. The process of claim 7, wherein $P^2$ is optionally substituted aralkyl.
10. A process for preparing a compound of formula (VII) or a salt thereof,

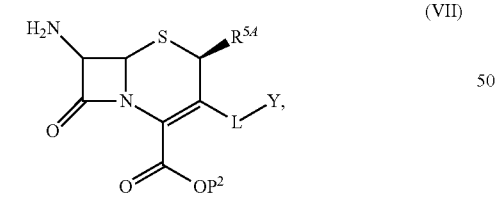

(VII)

wherein,
$R^{5A}$ is lower alkyl;
Y is halogen;
L is lower alkylene or lower alkenylene; and
$P^2$ is lower alkyl, alkylcarbonyloxymethyl in which the alkyl group is lower alkyl, optionally substituted aralkyl, or silyl groups,
which comprises:
deprotection of the compound of the formula (III) or a salt thereof obtained by the process according to claim 3, to give the compound of the formula (VII) or a salt thereof.

11. A compound of formula (II) or a salt thereof,

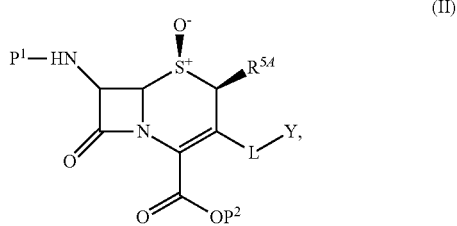

(II)

wherein
$R^{5A}$ is lower alkyl;
Y is halogen;
L is lower alkylene or lower alkenylene;
$P^1$ is acyl, phthalimide, optionally substituted aralkanoyl, optionally substituted aralkyl, optionally substituted arylimino, optionally substituted lower alkylimino, or tri-lower alkylsilyl; and
$P^2$ is lower alkyl, alkylcarbonyloxymethyl in which the alkyl group is lower alkyl, optionally substituted aralkyl, or silyl groups.

12. A compound of the formula (III) or a salt thereof,

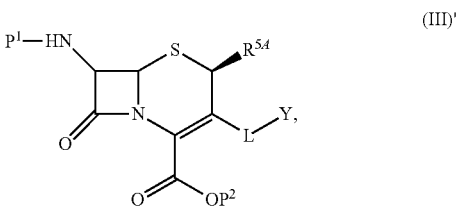

(III)' wherein
$R^{5A}$ is lower alkyl;
Y is halogen;
L is lower alkylene or lower alkenylene;
$P^1$ is acyl, phthalimide, optionally substituted aralkanoyl, optionally substituted aralkyl, optionally substituted arylimino, optionally substituted lower alkylimino, or tri-lower alkylsilyl; and
$P^2$ is lower alkyl, alkylcarbonyloxymethyl in which the alkyl group is lower alkyl, optionally substituted aralkyl, or silyl groups.

13. A compound of the formula (VII) or a salt thereof,

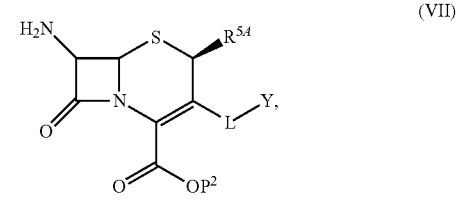

(VII)

wherein
$R^{5A}$ is lower alkyl;
Y is halogen;
L is lower alkylene or lower alkenylene; and
$P^2$ is lower alkyl, alkylcarbonyloxymethyl in which the alkyl group is lower alkyl, optionally substituted aralkyl, or silyl groups.

14. A compound of the formula (XVI) or a salt thereof,

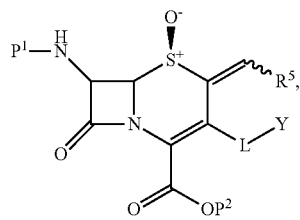
(XVI)

wherein

L is lower alkylene or lower alkenylene;

Y is halogen;

$R^5$ is hydrogen;

$P^1$ is acyl, phthalimide, optionally substituted aralkanoyl, optionally substituted aralkyl, optionally substituted arylimino, optionally substituted lower alkylimino, or tri-lower alkylsilyl;

$P^2$ is lower alkyl, alkylcarbonyloxymethyl in which the alkyl group is lower alkyl, optionally substituted aralkyl, or silyl groups; and the wavy line means that the bond is in cis or trans configuration, or a mixture thereof.

15. The compound according to claim 11, wherein L is —$CH_2$—; and $R^{5A}$ is methyl.

16. The compound according to claim 14, which is a crystal of following compound (XVI-2):

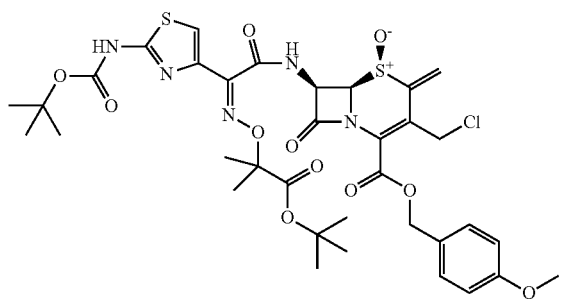
XVI-2 or solvate thereof.

17. The compound according to claim 16, which is a crystal having a diffraction pattern in powder X-ray diffraction showing main peaks at diffraction angle (2θ)=5.3±0.2°, 7.0±0.2°, 10.2±0.2°, 14.7±0.2°, 15.8±0.2°, 17.4±0.2°, 21.1±0.2°, and 21.3±0.2'.

18. The compound according to claim 11, which is a crystal of following compound (II-3):

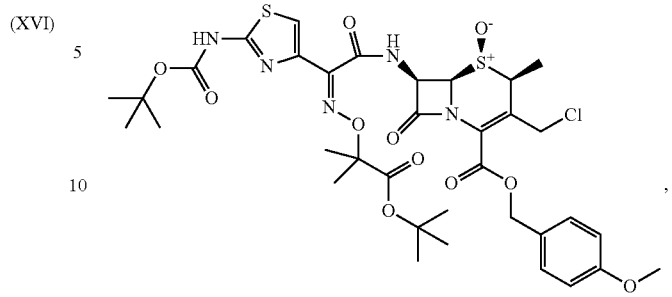
II-3 or solvate thereof.

19. The compound according to claim 18, which is a crystal having a diffraction pattern in powder X-ray diffraction showing main peaks at diffraction angle (2θ)=5.7±0.2°, 7.8±0.2°, 11.3±0.2°, 14.5±0.2°, 20.8±0.2°, and 21.6±0.2°.

20. The compound according to claim 12, which is a crystal of following compound (III-2):

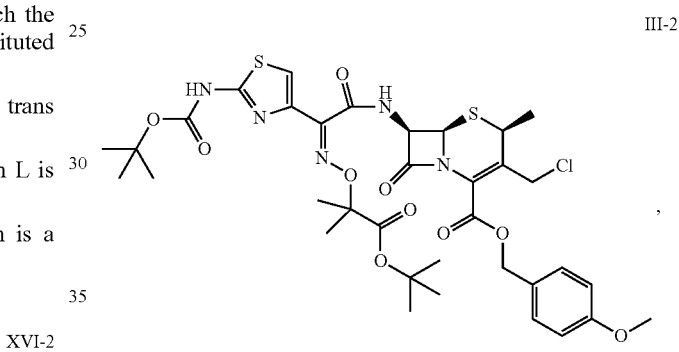
III-2 or solvate thereof.

21. The compound according to claim 20, which is a crystal having a diffraction pattern in powder X-ray diffraction showing main peaks at diffraction angle (2θ)=4.8±0.2°, 7.7±0.2°, 8.1±0.2°, 9.1±0.2°, 9.6±0.2°, 11.4±0.2°, 14.9±0.2°, 16.9±0.2°, 19.3±0.2°, and 20.2±0.2°.

22. The process of claim 3, wherein $R^{5A}$ is methyl.

23. The process of claim 4, wherein $R^{5A}$ is methyl.

24. The process of claim 5, wherein $R^{5A}$ is methyl.

25. The process of claim 6, wherein $P^1$ is acyl.

26. The process of claim 1, wherein $P^1$ is acyl.

27. The process claim 6, wherein $P^2$ is optionally substituted aralkyl.

28. The process claim 1, wherein $P^2$ is optionally substituted aralkyl.

29. The process claim 7, wherein $P^2$ is optionally substituted aralkyl.

30. The compound according to claim 12, wherein L is —$CH_2$—; and $R^{5A}$ is methyl.

31. The compound according to claim 13, wherein L is —$CH_2$—; and $R^{5A}$ is methyl.

* * * * *